United States Patent
Romano et al.

(12)
(10) Patent No.: US 6,852,511 B2
(45) Date of Patent: Feb. 8, 2005

(54) HEAT-INDUCIBLE PROMOTER

(75) Inventors: Ivano Romano, Wasenhaldenstrasse (CH); Gerd Gellissen, Ringstrasse (DE); Claudio DeVirgilio, Schafmattweg (CH)

(73) Assignee: Rhein Biotech, Gesellschaft für Neue Biotechnologische Prozesse und Produkte GmbH, Dusseldorf (DE)

( * ) Notice: Subject to any disclaimer, the term of this patent is extended or adjusted under 35 U.S.C. 154(b) by 0 days.

(21) Appl. No.: 09/927,811

(22) Filed: Aug. 9, 2001

(65) Prior Publication Data

US 2004/0086998 A1 May 6, 2004

Related U.S. Application Data

(63) Continuation of application No. PCT/EP00/01144, filed on Feb. 11, 2000.

(30) Foreign Application Priority Data

Feb. 11, 1999 (CH) .............................................. 0279/99

(51) Int. Cl.[7] ........................ C07H 21/04; C12N 15/11; C12N 15/63; C12N 1/21; C12N 1/19
(52) U.S. Cl. .................... 435/69.1; 536/23.1; 536/23.4; 536/24.1; 435/71.1; 435/320.1; 435/471; 435/70.1; 435/254.2; 435/254.11
(58) Field of Search ............................. 536/23.1, 23.4, 536/24.1; 435/69.1, 70.1, 71.1, 254.2, 254.11, 320.1, 471, 325, 252.3, 419

(56) References Cited

U.S. PATENT DOCUMENTS 5,792,921 A 8/1998 Londesborough et al.

OTHER PUBLICATIONS

Xia–Dong et al. Conservation of a stress response: human heat shock transcription factors functionally substitute for yeast HSF, Nov. 1, 1997. EMBO, 16(21): 6466–6477.*

Blazquez, Miguel A. et al., "Trehalose–6–P synthase is dispersable for growth on glucose but not for spore germination in *Schizosaccharomyces pombe*", J. Bacteriol. (1994), 176(13), 3895–3902.

Reinders, Anke et al., "The thermophilic yeast *Hansenula polymorpha* does not require trehalose synthesis for growth at high temperatures but does for normal acquisition of thermotolerance", J. Bacteriol. (1999), 181(15), 4665–4668.

Romano, I. "*Hansenula polymorpha* TPS1 gene", EMBL Database: Accession No. AJ010725, Mar. 2, 1999.

* cited by examiner

*Primary Examiner*—Gerry Leffers
*Assistant Examiner*—Ramin Akhavan
(74) *Attorney, Agent, or Firm*—Morgan, Lewis & Bockius, LLP

(57) ABSTRACT

The invention relates to nucleic acid molecules comprising a heat-inducible promoter and to expression vectors and host cells containing at least one nucleic acid molecule according to the invention. The present invention further relates to kits and methods for producing one or more proteins using the nucleic acid molecules according to the invention and to various uses of the same. The object of the invention is to provide a promoter the heat-inducible characteristic of which is as selective as possible, in particular a promoter which is active in yeasts and which is suitable for protein expression at high temperatures. This object is fulfilled by a nucleic acid molecule comprising a heat-inducible promoter of a *Hansenula polymorpha* gene coding for a protein with trehalose-6-phosphate-synthase activity;

21 Claims, 13 Drawing Sheets time (hours) after inoculation time (hours) after inoculation

TPS1 from

S. cerevisiae / K. lactis / C. albicans / S. pombe / A. higer

```
1001                                                                    1050
AGCGATGAAA TCGCAGACTT AC.TCTACAA CTGGTTCAGT AATTCTATTC
AGTGACGAAG TTGCTGATCT TC.ATTACAA CGGATTTTCC AACTCTATTC
AGTGATACGA TTGTGTGATTT AC.ATTATAA TGGGTTTTCA AATAGTATTT
GATGATGAGA CTGCCGACCG CC.ATTACAA CGGATTTAGT AACAGCATTC
CTGAAGGCGC TTGCTTGCTG ACGGATATCC ACTGCTCACA GACTCCATTC
```

```
1051                                                                    1100
TATTGGCCGTT ATTCCATTAC CATCCTGGTG AGATCAATTT CGACGAGAAT
TATTGGCCATT GTTCCATTAC CATCCTGGTG AGATCACTTT CGATGACACT
TATTGGCCACT TTTCCATTAT CATCCTGGTG AAATTGAACTT TGATGAAAAT
TTTGGCCCTT GTTCCACTAC CATCCTGGTG AAATTAATTT TGACGAGGAA
TTGGCCGCT GTTCCATTAC CATCCCGGTG AGATTACCTT TGACGAGTCC
```

```
1101                                                                    1150
GCGTGGTGG CATACAACGA GGCAAACCAG ACGTTCACCA ACGAGATTGC
GCATCGTTGG CGTACAACGA GGCAAATATG GCTTTTTCCG ATGAAATTGA
GAATGGGCAG CATATATTGA AGCCAATAAG AAATTTGCAT TGGAAATAGT
AATTGGGGAG CCTAACTGTGC GGCTAACTAC GCTTTTGCCG AGCCATTGT
GCCTGGGAAG CATACAAGGA GGCAAACCGT CTTTTTCGCA AAGCGGTTGC
```

```
1651                                                                    1700
GTTGGTGTCG ACAGGCTGGA TTCATCAAA GGTGTGCCTC AGAAGTTGAA
ATTGGGGTCG ATCGTCTTGA TTACATCAAA GTGTTCCTC AGAAGTTACA
GTTGGTGTTG ATAGATTAGA CTATATCAAA GTGTTCCGG GTGAAATTACA
GTGGGTGTTA ATCGTTTTGA CTACATTAAG GGTGTTCCCC AAAAATTACA
GTGGGTGTGG ACCGGCTGGA TTACATCAAA GTGTTCCCCC AGAAGTTACA
```

```
1701                                                                    1750
CGCCATGGAA GTGTTTCTGA ACGAGCATCC AGAATGGAGG GGCAAGGTTG
CGCCTTGGAA GTGTTCCTCG GTGCGCATCC TGAATGGATT GGTAAGGTGG
TGCATTTGAA GTCTTTTTGA ATGAAAATCC CGAAAATACCC GGCAAAGTAC
TGCCTTTGAA GTGTTCCTTAG AACAATACCC TGAATGGGTT GGAAAGGTAC
TGCCCTTGAG GTGTTCCTTA GCGATCATCC GGAGTGGGTT GGCAAGGTTG
``` conserved regions

FIG. 5

FIGUR 6

SEQ ID NO:8 (nucleic acid sequence)
SEQ ID NO:7 (amino acid sequence)

```
-792  CTTAAATACCACAATAGGAAAATTATCAATAAAGCTTTTCGGATTTCATTACGTTATATC  -733
-732  GCAAAAAAATAGTCGAGCTTTCTGAACCGTTCGTTAATAAAAAAATAGTTTTTTCAGATT  -673
-672  TCTATGTGAGGCAGTCACGATAGAATTCCATCGAACTCGTCAGCGCCAAATGTGAATGCG  -613
-612  GCTTTCAAAAGCTTTGTCGAATTTGGATGGGAATCCATGAATCGAAGATGTCAAAATGG   -553
-552  GGGATCACAAAAGTACACTCACGAGGAAAATCAAAACCTTCTCGTACCTTTAACACATAC  -493
-492  GGAAATGATCGATCGATTTGAGAAGATTCCTCAATGATTTTCGTCATATATAGGTATCTG  -433
-432  AGGTATTTATGGACCGATTCGTAATAACATCATATACATCGCGCTTTGTCCCTGTCCCAG  -373
-372  AGATTTCGATGAAAAAGCGAATTTTATTCTAATATTTGAAGCATGCCAAACATGGGGCA   -313
-312  GTTGATTTGTGTGAGGGTAAAATATCATGAATTGCACCCATCAAATGCAGCAAGATATTG  -253
-252  ACCAATCCTATAATAGAAAACAGACTTACCACAAATAGATTGTGATGACGATATTATGAA  -193
-192  TCTCCAGATGAAAGGCTCGAAAGCTATGAAGCCTCTTGAAACTTTTCATGGTGAGATAAT  -133
-132  ATTTTCGAAATTTCCACGAACTTCTAAAACGCAATTATTGAATATAAAGGAAAAATAATA  -73
 -72  TTTCCATATAGCAAGCAAATCAAGCTGCACTCCTCATCCTTAAAACTAATAAATCTTACC  -13
 -12  CATTTGATACCAATGGTCAAAGGTAATGTTATAGTGGTTTCAAATAGAATCCCAGTCACT  48
   1           MetValLysGlyAsnValIleValValSerAsnArgIleProValThr       16

49  ATTAAGAAGACTGAAGATGATGAAAATGGAAAATCAAGATACGACTATACAATGTCATCA  108
  17  IleLysLysThrGluAspAspGluAsnGlyLysSerArgTyrAspTyrThrMetSerSer   36

109  GGCGGATTAGTGACGGCATTACAAGGGCTCAAAAATCCATTTCGATGGTTTGGATGGCCT  168
  37  GlyGlyLeuValThrAlaLeuGlnGlyLeuLysAsnProPheArgTrpPheGlyTrpPro   56

169  GGGATGTCTGTTGATAGCGAACAGGGACGACAAACTGTCGAGCGGGATTTGAAGGAAAAG  228
  57  GlyMetSerValAspSerGluGlnGlyArgGlnThrValGluArgAspLeuLysGluLys   76

229  TTCAATTGTTATCCGATATGGTTAAGTGACGAAATTGCAGACTTACATTATAACGGCTTT  288
  77  PheAsnCysTyrProIleTrpLeuSerAspGluIleAlaAspLeuHisTyrAsnGlyPhe   96

289  AGCAATTCTATACTTTGGCCATTGTTCCACTATCACCCAGGGGAGATGAATTTTGATGAA  348
  97  SerAsnSerIleLeuTrpProLeuPheHisTyrHisProGlyGluMetAsnPheAspGlu  116

349  ATTGCTTGGGCCGCTTATTTGGAAGCAAATAAACTGTTTGCCAAACGATCTTAAAGGAG   408
 117  IleAlaTrpAlaAlaTyrLeuGluAlaAsnLysLeuPheCysGlnThrIleLeuLysGlu  136

409  ATAAAAGACGGGGACGTTATCTGGGTACATGATTATCATCTCATGTTGTTGCCTTCACTG  468
 137  IleLysAspGlyAspValIleTrpValHisAspTyrHisLeuMetLeuLeuProSerLeu  156

469  CTAAGAGACCAACTTAATAGTAAGGGGCTACCGAATGTCAAAATTGGCTTTTTCCTTCAT  528
 157  LeuArgAspGlnLeuAsnSerLysGlyLeuProAsnValLysIleGlyPhePheLeuHis  176

529  ACTCCTTTTCCTTCAAGCGAAATATACAGGATACTTCCTGTAAGGAAAGAAATTCTCGAA  588
 177  ThrProPheProSerSerGluIleTyrArgIleLeuProValArgLysGluIleLeuGlu  196

589  GGAGTGCTTAGTTGTGATTTGATAGGTTTCCACACCTATGATTATGTCCGTCACTTTCTT  648
 197  GlyValLeuSerCysAspLeuIleGlyPheHisThrTyrAspTyrValArgHisPheLeu  216

649  AGTTCGGTTGAAAGAATATTGAAATTGCGAACGAGCCCACAAGGTGTTGTCTATAATGAT  708
 217  SerSerValGluArgIleLeuLysLeuArgThrSerProGlnGlyValValTyrAsnAsp  236
```

FIGUR 6
(cont.)

```
 709  AGACAGGTGACTGTAAGTGCTTATCCGATTGGCATTGACGTTGACAAATTCTTGAATGGT   768
 237  ArgGlnValThrValSerAlaTyrProIleGlyIleAspValAspLysPheLeuAsnGly   256

769  CTTAAGACTGATGAGGTCAAAAGCAGGATAAAACAGCTGGAAACCAGATTTGGTAAAGAT   828
 257  LeuLysThrAspGluValLysSerArgIleLysGlnLeuGluThrArgPheGlyLysAsp   276

829  TGTAAACTTATTATTGGGGTGGACAGGCTGGATTACATCAAAGGTGTACCTCAAAAACTC   888
 277  CysLysLeuIleIleGlyValAspArgLeuAspTyrIleLysGlyValProGlnLysLeu   296

889  CACGCGTTTGAAATTTTCTTGGAGAGACACCCTGAGTGGATTGGAAAAGTTGTTTTGATA   948
 297  HisAlaPheGluIlePheLeuGluArgHisProGluTrpIleGlyLysValValLeuIle   316

949  CAGGTGGCTGTCCCCTCACGAGGGGACGTTGAAGAATATCAATCTTTGAGGGCAGCTGTA  1008
 317  GlnValAlaValProSerArgGlyAspValGluGluTyrGlnSerLeuArgAlaAlaVal   336

1009  AATGAGCTAGTGGGAAGAATCAATGGTAGATTTGGTACCGTCGAATTTGTTCCTATCCAT  1068
 337  AsnGluLeuValGlyArgIleAsnGlyArgPheGlyThrValGluPheValProIleHis   356

1069  TTCCTTCATAAAAGCGTGAACTTCCAAGAGCTGATATCTGTCTACGCTGCTAGTGATGTT  1128
 357  PheLeuHisLysSerValAsnPheGlnGluLeuIleSerValTyrAlaAlaSerAspVal   376

1129  TGTGTAGTGTCATCGACACGGGACGGAATGAATTTGGTCAGTTATGAATACATTGCTTGT  1188
 377  CysValValSerSerThrArgAspGlyMetAsnLeuValSerTyrGluTyrIleAlaCys   396

1189  CAACAAGATCGAAAGGGATCTCTAGTACTAAGTGAATTTGCGGGAGCTGCTCAGTCATTA  1248
 397  GlnGlnAspArgLysGlySerLeuValLeuSerGluPheAlaGlyAlaAlaGlnSerLeu   416

1249  AATGGCGCTCTCGTAGTGAATCCATGGAATACAGAAGAACTCAGTGAAGCTATTTACGAA  1308
 417  AsnGlyAlaLeuValValAsnProTrpAsnThrGluGluLeuSerGluAlaIleTyrGlu   436

1309  GGCTTGATCATGAGTGAAGAGAAAAGGAGGGGCAATTTTCAGAAGATGTTCAAGTACATT  1368
 437  GlyLeuIleMetSerGluGluLysArgArgGlyAsnPheGlnLysMetPheLysTyrIle   456

1369  GAGAAATATACTGCAAGTTATTGGGGAGAGAACTTTGTGAAAGAATTGACGAGAGTGTGA  1428
 457  GluLysTyrThrAlaSerTyrTrpGlyGluAsnPheValLysGluLeuThrArgVal     476

1429  TTACTGTGGTTTGCAGGTTAATTTGAAATGTTCACTTGTACTTGAAGAATTTTATATTAT  1488
1489  ATACATGTTATACATCAATAGGATAAAAATTAAGTAGACAAAGTTATCATTTTGTTGGGC  1548
1549  TGTAAAAATTGAACGATAACAATATATTTGACAAAATTAATTTGATCTAATTGAGCTGGA  1608
1609  GGGCGTAATATATTTGGTTTCCTGAATCATCTTGTAGATCACAATATGGGGCAGCTTCTT  1668
1669  TCGCAGCCGATCACAGAGAAACACATCACACTTGTCCAACATGATCACATATCGCATTCA  1728
1729  ATCGGGGAAATGCAAGGATACAGGTTGACCATGGAAGACGCGTTCTGTGATTTGAACGAA  1788
1789  AGAATATTCGTGACGGAAGAGGGACTTGACATCAGAAAACAAGACGAGAATACAGAGGGT  1848
1849  GATCTGGAGTCTCTTCAAATTAACATTTATGGTGTCTTTGACGGACATGGCGGTT       1903
```

HEAT-INDUCIBLE PROMOTER

This is a continuation of PCT/EP00/01144 filed Feb. 11, 2000.

The present invention relates to nucleic acid molecules comprising a heat-inducible promoter, as well as to expression vectors and host cells containing at least one nucleic acid molecule according to the invention. The present invention further relates to kits and methods for the production of one or more proteins using the nucleic acid molecules according to the invention and to various uses of the same.

Microorganisms are able to respond to a number of stress situations, such as heat or cold shock, ethanol, heavy-metal ions, oxygen deprivation, or nutrient deprivation, in particular glucose deprivation. Yeasts and other fungi are known to accumulate trehalose during phases of reduced growth. These are generally the stages of development which, for example, are tolerant of water deprivation and heat, such as spores, conidiae, sclerotia, or cells in the stationary growth phase. It is also already known that *Saccharomyces cerevisiae* cells accumulate trehalose during a one-hour heat shock from 27° C. to 40° C. and that the trehalose accumulation correlates to an increased thermotolerance. Selective mutations have been used to demonstrate that trehalose is indeed a necessary factor for the induction of thermotolerance.

HSEs (heat shock elements) and STREs (stress responsive elements) are present in the promoter regions of stress-induced genes, such as the genes of *S. cerevisiae* responsible for the trehalose synthesis. These elements appear to mediate activation of stress genes by stress induction, including heat shock induction. It is now generally accepted that phosphorylation of Msn2p and Msn4p via the Ras/cAMP pathway inhibits the Msn2p and Msn4p transcription factors. In the absence of this inhibition (e.g. under stress conditions) Msn2p and Msn4p become active. STREs with the sequence CCCCT are attributed with a role in the response to the stress conditions.

Owing to their ability to perform cotranslational and posttranslational modifications which are similar to the human modifications, fungi, and in particular yeasts, are attractive systems for the production of recombinant proteins. For the production of recombinant proteins the coding sequence of a gene which encodes a protein of interest is often expressed under the control of a suitable heterologous promoter. The so-called inducible promoters which can be induced by particular environmental conditions have proved particularly advantageous for this purpose. The promoters of genes which encode key enzymes in the methylotrophic metabolism, such as the MOX (methanol oxidase) or the FMD (formate dehydrogenase) promoter, for example, offer widely exploitable possibilities for an heterologous gene expression which is regulated strongly by the carbon source.

Expression vectors have been produced for research in molecular biology which comprise a heat-inducible promoter, for example that of the hsp70 gene from Drosophila. The promoters employed in the past for heat shock induction in fungal cells and in particular in yeasts have the drawback that they do not respond selectively to heat shock. Their mechanism of activation and deactivation cannot therefore be controlled sufficiently well, which can cause problems in particular during the production of proteins which are damaging to cells. The TPS1 promoter from *S. cerevisiae*, for example, exhibits several sequences known to be general stress elements (STRE elements), namely CCCCT and AGGGG, but no more than one sequence acting as a heat-shock element (HSE), namely GGAACAGAACAATCG. In addition, owing to their wide stress response, the promoters currently known are activated by a stress factor to a degree which is not satisfactory for many applications.

The object of the invention is therefore to provide a promoter the heat-inducible characteristic of which is as selective as possible, specifically a promoter which is active in fungi and in particular in yeasts, and which is suitable for protein expression at high temperatures.

According to the invention, this object is achieved by a nucleic acid molecule comprising a heat-inducible promoter and which is selected from the following nucleic acids:
(a) a nucleic acid the sequence of which comprises the promoter sequence of a *Hansenula polymorpha* gene coding for a protein with trehalose-6-phosphate synthase activity;
(b) a nucleic acid with the sequence indicated in SEQ ID NO:1;
(c) a nucleic acid with a sequence which exhibits at least 40% identity over a length of 300 bp with one of the sequences indicated in (a) or (b);
(d) a nucleic acid which hybridizes to the complementary strand of one of the nucleic acids indicated in (a), (b) or (c);
(e) a derivative of one of the nucleic acids indicated in (a), (b) or (c) obtained by substitution, addition and/or deletion of one or more nucleotides;
(f) a fragment of one of the nucleic acids indicated in (a) to (e) which retains the function of the heat-inducible promoter;
(g) a combination of several of the nucleic acids indicated in (a) to (f), wherein the sequences of the nucleic acids may be different or the same; or
by a nucleic acid molecule the sequence of which is complementary to the sequence of one of the nucleic acids indicated in (a) to (g).

The term "heat-inducible promoter", as employed in this context, refers to a nucleic acid sequence which, at a temperature rise in the culture medium from 25° C. to at least 37° C., preferably to 47° C., brings about an increase of at least 50% in the transcription (RNA synthesis) of a gene under the transcriptional control of the promoter.

"Trehalose-6-phosphate synthase activity " refers to the conversion of glucose-6-phosphate (Glu6P) and UDP-glucose (UDPG) to trehalose-6-phosphate and UDP, which is catalyzed by the enzyme trehalose-6-phosphate synthase (TPS). The trehalose-6-phosphate synthase activity of a protein or polypeptide can be measured for example by the method described below under "Materials and Methods".

The feature "sequence which hybridizes to the complementary strand of one of the nucleic acids indicated in (a), (b) or (c)" refers to a sequence which hybridizes under stringent conditions with the complementary strand of a nucleic acid having the features indicated in (a), (b) or (c). For example, hybridization may be performed at 68° C. in 2×SSC or according to the protocol of the Dioxygenin labelling kit manufactured by Boehringer (Mannheim). A further example of stringent hybridization conditions is incubation at 65° C. overnight in 7% SDS, 1% BSA, 1 mM EDTA, 250 mM sodium phosphate buffer (pH 7.2) followed by washing at 65° C. with 2×SSC, 0.1% SDS.

The term "% identity", as known in the art, refers to the degree of similarity between the sequences of two or more DNA molecules or of two or more polypeptide molecules, as determined by a comparison of the sequences. The percentage of the "identity" results from the percentage of identical regions in two or more sequences in consideration of gaps or other particular sequence features.

The identity of related DNA molecules or polypeptides can be determined by means of known procedures. In the main, dedicated computer programs are employed using algorithms which make allowance for the particular requirements. Preferred methods for determination of the identity first generate the greatest matches between the sequences studied. Computer programs for determining the identity between two sequences include, but are not limited to, the GCG program package, including GAP (Devereux, J., et al., Nucleic Acids Research 12 (12): 387 (1984); Genetics Computer Group University of Wisconsin, Madison, (Wis.)); BLASTP, BLASTN and FASTA (Altschul, S. et al., J. Molec Biol 215:403/410 (1990)). The BLAST X program can be obtained from the National Centre for Biotechnology Information (NCBI) and from other sources (BLAST Manual, Altschul S., et al., NCB NLM NIH Bethesda Md. 20894; Altschul, S., et al., J. Mol. Biol. 215:403/410 (1990)). The well known Smith Waterman algorithm may also be used to determine identity.

Preferred parameters for sequence comparison comprise the following:

| Algorithm: | Needleman and Wunsch, J. Mol. Biol 48:443–453 (1970) |
|---|---|
| Comparison matrix: | Matches = +10, Mismatches = 0 |
| Gap penalty: | 50 |
| Gap length penalty: | 3 |

The GAP program is also suitable for use with the above parameters. The above parameters are the default parameters for nucleic acid sequence comparisons.

Other algorithms, gap opening penalties, gap extension penalties, comparison matrices including those set forth in the Program Manual, Wisconsin Package, Version 9, September 1997, may be employed. The choices to be made will depend upon the specific comparison to be made, and additionally whether the comparison is between pairs of sequences, in which case GAP or Best Fit are preferred, or between one sequence and a large database of sequences, in which case FASTA or BLAST are preferred.

Surprisingly, the nucleic acid molecules according to the invention, and in particular the promoter of the trehalose-6-phosphate synthase (TSP1) gene of *Hansenula polymorpha*, have now been found to contain, at least in the first 300 bp upstream of the coding sequence, none of the STRE elements which were found in *S. cerevisiae* and which were assumed to be primarily responsible for the stress response including heat-shock induction of this gene. This promoter was further found to respond well and very selectively to heat.

The nucleic acid molecules according to the invention may either be prepared synthetically by conventional methods, or isolated from suitable DNA libraries and subsequently mutated as required. The preparation of such libraries is also known in the art. Isolation is preferably performed by preparing a probe with a length of at least 200–400 bp of the coding sequence of the TPS1 gene of *H. polymorpha* (see FIG. 6), which is used to screen a DNA library, in particular a genomic DNA library. A probe of this kind can be prepared by means of PCR (polymerase chain reaction) using suitable primers, each of which should preferably be at least 20–21 bp in length and possess suitable sequences according to FIG. 6 (or the corresponding complementary sequence), and genomic DNA or cDNA from *H. polymorpha* as a "template".

Probes may either be synthesized, or prepared by fragmentation of available TPS1 DNA where applicable. It is of course also possible to screen directly by means of probes that correspond to parts of the promoter sequence; this procedure is less preferable, however, owing to the at best incomplete conservation of the sequence within non-coding parts.

In an embodiment of the nucleic acid molecules according to the invention, the sequence of the nucleic acid exhibits at least 60%, preferably at least 80% identity over a length of 300 bp with one of the sequences indicated above under (a) or (b).

Nucleic acid molecules which comprise a heat-inducible promoter and which exhibit at least 90% identity over a length of 300 bp with one of the sequences indicated above under (a) or (b) are particularly preferred. Most preferred are however nucleic acid molecules which exhibit at least 95% identity over a length of 300 bp with one of the sequences indicated above under (a) or (b).

Nucleic acid molecules preferred for carrying out the invention exhibit at least one heat shock element with the sequence NGAANNNNNNNGAAN (SEQ ID NO:2) or the complementary sequence thereof, wherein the nucleotides denoted by N may be A, T, C and G independent of each other. The nucleic acid molecules according to the invention preferably exhibit at least one heat shock element with the sequence NGAANNBWMNNNGAAN (SEQ ID NO:3) or the complementary sequence thereof, wherein B is a G, C or T, W an A or T, and M a C or A.

In a particularly preferred embodiment of the invention, the heat shock element is selected from TGAAGCCTCT-TGAAA (SEQ ID NO:4) and/or TGAATATAAAGGAAA (SEQ ID NO:5) and/or the complementary sequences thereof, wherein two or more heat shock elements, where present, may exhibit the same or different sequences. A preferred nucleic acid molecule according to the invention exhibits at least two different heat shock elements.

In a preferred embodiment of the invention, the nucleic acid molecules according to the invention do not contain an STRE element having the sequence CCCCT or AGGGG.

The invention also provides fragments of the nucleic acid molecules according to the invention as stated above which retain the function of the heat-inducible promoter. A fragment comprising the sequence from nucleotide 228 to nucleotide 792 in the SEQ ID NO:1 is particularly preferred. A further preferred fragment comprises the sequence from nucleotide 493 to nucleotide 792 in the SEQ ID NO:1. A fragment comprising the sequence from nucleotide 627 to nucleotide 713 in the SEQ ID NO:1 may also be used.

The nucleic acid molecules according to the invention may further comprise at least one nucleic acid sequence for a heterologous gene under the transcriptional control of the heat-inducible promoter.

A "heterologous gene" shall refer to the coding part of a structural gene which is either not expressed under control of its own (homologous) promoter, or is not expressed in the organism from which the gene derives, or is expressed neither under the control of the original promoter nor in the original organism.

In a further embodiment of the invention, the nucleic acid molecules according to the invention comprise a nucleic acid sequence under the transcriptional control of the heat-inducible promoter which is selected from the following sequences:

(i) a nucleic acid sequence which encodes a polypeptide with the amino acid sequence of the trehalose-6-phosphate synthase of *Hansenula polymorpha*;

(ii) a nucleic acid sequence as indicated in SEQ ID NO:6;
(iii) a nucleic acid sequence which exhibits at least 80% identity with the sequence indicated in SEQ ID NO:6;
(iv) a nucleic acid sequence which encodes a polypeptide with the amino acid sequence indicated in SEQ ID NO:7 or with a partial sequence thereof, wherein the polypeptide exhibits trehalose-6-phosphate synthase activity;
(v) a nucleic acid sequence which in consideration of the degeneration of the genetic code would code a polypeptide with the amino acid sequence indicated in SEQ ID NO:7 or with a partial sequence thereof, wherein the polypeptide exhibits trehalose-6-phosphate synthase activity;
(vi) a nucleic acid sequence which encodes a polypeptide the amino acid sequence of which exhibits at least 80% identity with the amino acid sequence indicated in SEQ ID NO:7.

The nucleic acid sequence indicated under (iii) preferably exhibits at least 90% identity with the sequence indicated in SEQ ID NO:6. In an alternative form of the nucleic acid molecules according to the invention, the nucleic acid sequence indicated under (vi) encodes a polypeptide the amino acid sequence of which exhibits at least 90% identity with the amino acid sequence indicated in SEQ ID NO:7.

The nucleic acid molecule according to the invention may further comprise a nucleic acid sequence encoding a signal peptide which ensures export of the expressed protein, wherein the nucleic acid sequence encoding the signal peptide is preferably bound directly to the heterologous gene to be expressed. The secretion and modification of many eukaryotic proteins requires that the N-terminus of the protein sequence be fused with a signal sequence, in order to direct the polypeptides into the secretion apparatus. Components from the *S. occidentalis* gene GAM1 and from a hormonal gene of the crab *Carcinus maenas*, which have been used successfully for the secretion of hirudin (Weydemann et al., 1995), may for example be considered here. The nucleic acid molecule according to the invention may further comprise a terminator element containing signal structures for the RNA polymerase which lead to termination of the transcription. Examples of terminator elements which may be employed are the MOX or the PHO1 terminator of *H. polymorpha*.

A further subject matter of the invention is a host cell containing at least one nucleic acid molecule according to the invention, wherein the host cell is a prokaryotic or eukaryotic cell. The eukaryotic cell may for example be a plant cell. The eukaryotic cell is preferably a fungal cell, a yeast cell is particularly preferred. Fungi are given particular consideration as host cells for carrying out the present invention, for example filamentous fungi such as *Aspergillus, Neurospora, Mucor, Trichoderma, Acremonium, Sordaria* and *Penicillium* or yeasts such as *Saccharomyces, Hansenula, Pichia, Kluyveromyces, Schwanniomyces, Yarrowia, Arxula, Trichosporon* and *Candida*.

In the most preferred embodiment of the invention the yeast cell is a facultative methylotrophic Hansenula yeast, preferably *Hansenula polymorpha*. *H. polymorpha* is a thermotolerant yeast cell and belongs to the small group of the so-called methylotrophic yeasts which are capable of using methanol as carbon and energy source. *H. polymorpha* was isolated from soil samples by incubation at 37° C. (Levine and Cooney, 1973). The high temperature at which *H. polymorpha* continues to grow and produce protein enables other undesired organisms to be eliminated. The reason for this is that *H. polymorpha* has been shown not only to possess a very high optimum growth temperature, in the region of 37° C., but also to be able to survive temperatures of approximately 50° C. unharmed (see FIG. 1). The vitality of *H. polymorpha* following entry into the stationary phase does not fall for some 50 hours even at 47° C. (FIG. 2).

A further subject matter of the present invention is an expression vector comprising at least one nucleic acid molecule according to the invention. Such expression vector may also contain other nucleic acid sequences in addition to the heat-inducible promoter, for example a sequence which encodes a polypeptide, a selection marker gene, an origin of replication for *E. coli*, etc.

The present invention also provides a kit comprising:
(a) an expression vector according to the invention which is suitable for having cloned into it a nucleic acid which encodes a recombinant protein, and
(b) a host cell suitable for induction of the heat-inducible promoter and for production of the recombinant protein.

"Cloning" is to comprise all cloning methods known in the art which could be employed for this purpose. These methods are not all described here individually, being familiar to a person skilled in the art.

The invention further provides a kit comprising
(a) an expression vector, and
(b) a host cell suitable for induction of the heat-inducible promoter and for production of a protein encoded by a coding sequence under the transcriptional control of the heat-inducible promoter.

The nucleic acid molecules, host cells, expression vectors and kits according to the invention may be used for recombinant expression of a gene under the control of the heat-inducible promoter, or for production of one or more proteins.

"Recombinant expression in a suitable host cell" shall refer to all expression methods known in the state of the art in known expression systems which could be used for this purpose. These methods are not all described here individually, being familiar to a person skilled in the art.

A further subject matter of the invention is a method for the production of one or more proteins, said method comprising:
(i) cloning at least one nucleic acid encoding a recombinant protein into an expression vector according to the invention, such that the nucleic acid thus cloned is under the transcriptional control of the heat-inducible promoter;
(ii) introduction of the expression vector obtained in (i) into a host cell suitable for induction of the heat-inducible promoter and for production of the recombinant protein;
(iii) cultivation of the host cell obtained in (ii);
(iv) induction of the heat-inducible promoter by methods known per se.

Should the expression vector according to the invention contain a sequence encoding a polypeptide and being under the transcriptional control of the heat-inducible promoter, the method according to the invention for production of one or more proteins comprises the following steps:
(i) introduction of an expression vector into a host cell suitable for induction of the heat-inducible promoter and for production of the recombinant protein;
(ii) cultivation of the host cell obtained in (i);
(iii) induction of the heat-inducible promoter by methods known per se.

BRIEF DESCRIPTION OF THE DRAWINGS

The invention is now described in closer detail with reference to the figures, which show the following:

FIG. 5 shows the homology of certain DNA sequence regions of trehalose-6-phosphate synthase from a number of organisms. including *S. cerevisiac* (SEQ ID NO:29). *K. lactis* (SEQ ID NO:30). *C. albicans* (SEQ ID NO:31), *S. pombe* (SEQ ID NO:32) and *A. niger* (SEQ ID NO:33).

FIG. 6 shows the DNA sequence of the TPS1 gene of *H. polymorpha* (SEQ ID NO:8) and the derived amino acid sequence (SEQ ID NO:6). The heat shock elements in the promoter sequence are underlined.

EXAMPLES

Figure 1:
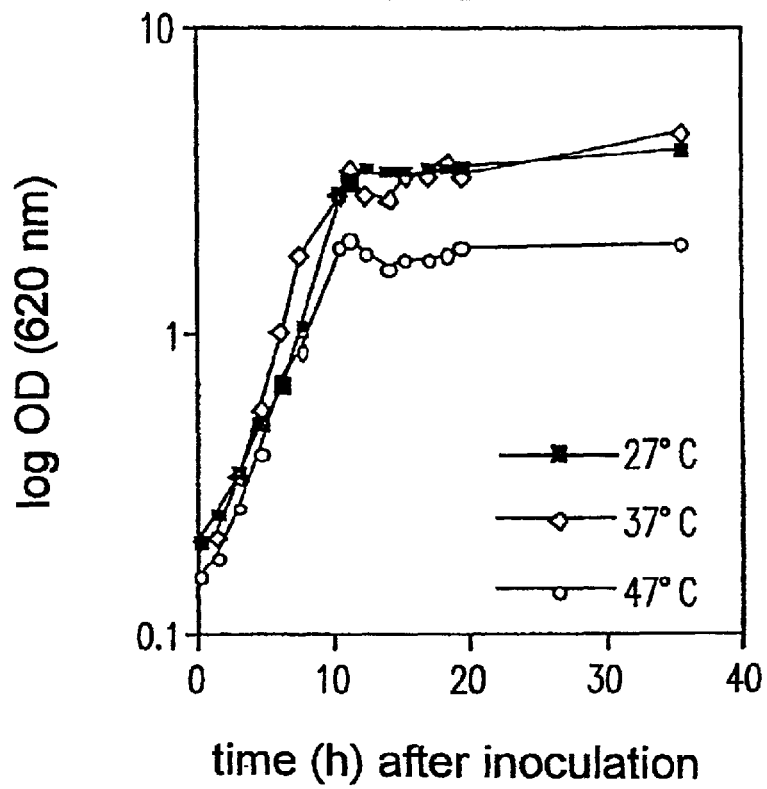
FIG. 1 shows growth curves of *H. polymorpha* at 27° C., 37° C. and 47° C.
Figure 2:
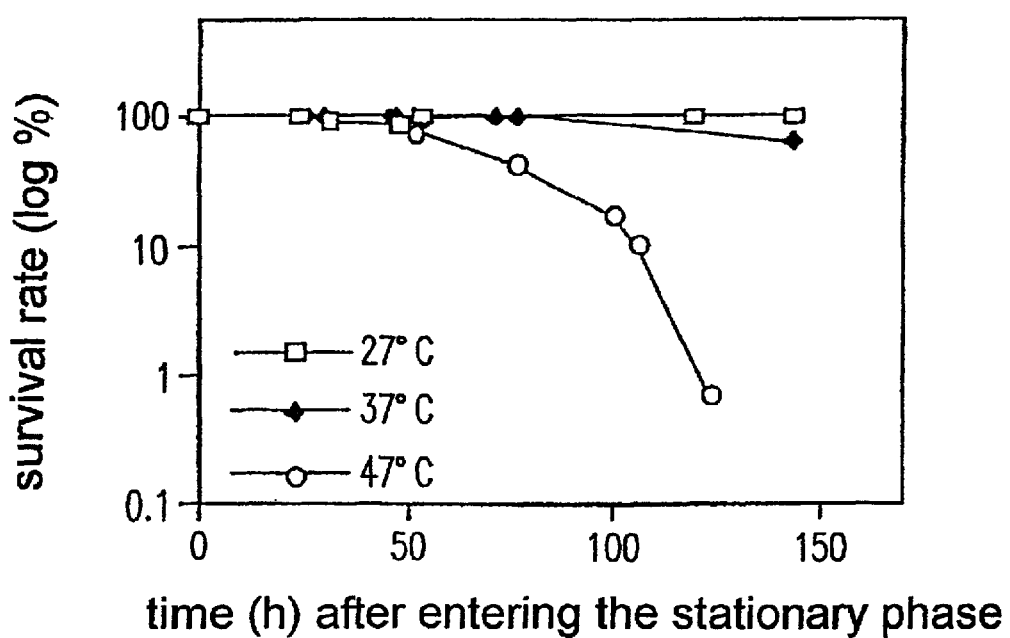
FIG. 2 shows the vitality following entry into the stationary phase at 27° C., 37° C. and 47° C.

Materials and Methods:

| Special reagents and materials | |
|---|---|
| Bio 101, Vista, USA | Geneclean II Kit |
| BioRad Lab., Munich, Germany | BioRad Protein Assay (Bradford) |
| Boehringer, Mannheim, Germany | GOD/POD kit for glucose measurement, ethanol kit, "COMPLETE" proteinase inhibitor cocktail tablets |
| Fluka Chemie AG, Buchs, Switzerland | Cycloheximide (Actidion), SDS, D + trehalose, PEP, TRICIN, NADH, Folin-Ciocalteu phenol reagent |
| ICN Biochemicals, Ohio, USA | "Liquigel" 40% acrylamide/N'N'-methylene-bisacrylamide (37.5:1) |
| Kodak, New York, USA | BIOMAX MR scientific imaging film |
| Mediatech, Herndon, USA | Geneticin G418 sulphate (antibiotic) |
| Perkin Elmer Applied Biosystems, Forest City, USA | DNA sequencing kit |
| Pharmacia Biotech, Sweden | Nap-10 columns (with Sephadex G-25), all restriction enzymes used, Taq polymerase |
| Qiagen GmbH, Germany | Plasmide Midi Kit (50) |
| Schleicher + Schuell, Dassel, Germany | Protran BA 83 0.2 μm/Ø 82 mm (cellulose nitrate round filter), Protran BA 83 0.2 μm (transfer membrane for blots) |
| Sigma, St. Louis, USA | Monoclonal goat anti-rabbit immunoglobulins (alkaline phosphatase conjugate), trehalase from pig kidneys (Cat. No. T-8778), UDPG, glucose-6-P, LDH, pyruvate kinase |
| Stratagene, La Jolla, USA | Prime-It II kit (random primer labelling kit), NucTrap columns (probe purification columns incl. push column beta shield device) |
| US Biological, Swampscott, USA | Bacteriological Agar, YPD broth enhanced formulation W/Peptone X, LB broth Miller |

-continued

| Apparatus used | |
|---|---|
| Electroporation unit | E. coil pulser, BioRad Laboratories, Hercules USA |
| HPLC | DIONEX DX-300, DIONEX, Sunnyvale, USA |
| Cooling centrifuges | Centrikon H-401, Kontron Instr. AG, Zürich, Switzerland |
| | IEC Centra GP8R, Brouwer, Lucerne, Switzerland |
| | Biofuge 17RS, Heraeus Sepatech, Germany |
| PCR apparatus | Progene, Techne, Cambridge, United Kingdom |
| Phosphoimager | GS 250 Molecular Imager (including associated equipment), BioRad Laboratories, Hercules, USA |
| Photometer | Anthos 2001 (for microtiter plates), Anthos Labtec Instruments, Salzburg, Austria |
| | Shimadzu UV-160A, Japan |
| Sequencer | ABI PRISM 301 Genetic Analyzer, Perkin Elmer, Applied Biosystems, Foster City, USA |

Bacterial Strain and Culture Conditions

The *E. coli* strain DH5α (F' endA1hsdR 17$r_k m_k$+ supE44thi-1recA1gyra relA(lacZYA-argF) U169(φ80Δ (lacZ)M15) (Gibco BRL, Gaithersburg Md., USA) was employed for cloning of the TPS1 gene of *H. polymorpha*, the standard protocols (Sambrook et. al., 1989) being followed. The medium for *E. coli* was also produced in accordance with a standard recipe (Sambrook et al., 1989).

Isolation of Plasmid DNA from *E. coli* (STET Prep)

Plasmid DNA was isolated in accordance with a modified protocol according to Sambrook et al. (1989). A spatula was used to scrape cell material from a plate. This material was then added to 500 μl STET (8% [w/v] sucrose, 5% [v/v] Triton X-100, 50 mM EDTA, 50 mM Tris-HCl, pH 8.0) with 35 μl lysozyme (10 mg/ml) and mixed. The samples were then boiled for 1 min 40 s at 100° C. and centrifuged for 10 minutes at 20,000 g and 4° C. Approx. 400 μl of supernatant was drawn by means of a pipette, and the DNA precipitated using 400 μl isopropanol. Following centrifugation for 10 minutes at 20,000 g and 4° C., the entire supernatant was discarded and the DNA pellet washed once with ice-cold 70% [v/v] ethanol. Finally, the DNA was dried at room temperature and suspended in 50–70 μl TE (10 mM Tris-HCl, pH 8.0, 1 mM EDTA, pH 8.0).

Yeast Strain and Culture Conditions

The yeast strain employed was a wild-type *Hansenula polymorpha* (made available by P. Piper, London (1994)). Stock cultures were grown on YPD Agar (2% [w/v] glucose, 2% [w/v] bactopeptone, 1% [w/v] yeast extract, 2% [w/v] agar) and re-stocked every six weeks. They served as inoculum for YPD liquid cultures (composition the same as YPD agar, but without 2% [w/v] agar).

The strain *H. polymorpha* RB11 (odc1 orotidine-5-phosphate-decarboxylase-deficient (uracil-auxotrophic) *H. polymorpha* strain (Weydemann et al., 1995)) was used for the experiments in Examples 3 and 4. The full medium employed contained 2% glucose or glycerine, 1% yeast extract and 2% bactopeptone; the selection medium contained 0.17% yeast nitrogen base, 0.5% ammonium sulphate, 2% glucose or glycerine, 38.4 mg/l arginine, 57.6 mg/l isoleucine, 48 mg/l phenylalanine, 57.6 mg/l valine, 6 mg/ml threonine, 50 mg/l inositol, 40 mg/l tryptophan, 15 mg/l tyrosine, 60 mg/l leucine, 4 mg/l histidine. Uracil is not present in the selective medium.

For the cultivation of cell cultures, autoclaved liquid media were inoculated with stock culture and incubated overnight in shaking incubators at 27° C., 37° C. or 47° C., depending upon the experiment.

Determination of the Optical Density of the *H. polymorpha* Cell Cultures

In order to determine the optical density (OD), 200 μl (suitably diluted where applicable with YPD) cell culture was placed in a vial of a microtitre plate and measured at 620 nm using an Anthos 2001 photospectrometer. 200 μl YPD was employed as the blank.

Growth and Heat Shock Experiments with *H. polymorpha*

Overnight cultures were used to inoculate YPD medium in Erlenmeyer flasks. Care was taken to inoculate this preculture at the temperature at which the experiment itself was later begun (27° C. for heat shocks, 27° C., 37° C. or 47° C. for growth experiments).

The cultures were inoculated to an initial $OD_{620}$ of 0.2 for each growth experiment, and maintained continuously in shaking incubators (Multitron). Conversely, the cultures were inoculated to an initial OD of 0.05 for heat shock experiments. The culture was allowed to grow at 27° C. up to an $OD_{620}$ of 0.4 (approx. 1–1.5×10$^8$ cells per ml of culture) before performance of the heat shock to 47° C. in a water bath with shaking function (Aquatron). Samples were then taken over a further two hours. The cell culture was then cooled in a second water bath for one hour to 27° C.

Transformation of *H. polymorpha* by Electroporation 100 ml of YPD was inoculated with 5 ml of a densely grown overnight culture. The culture was shaken at 37° C. for approximately three hours to an $OD_{600}$ of 0.8–1.2. The cells were harvested by centrifugation at 3,000 rpm and resuspended in 20 ml $Kp_i$ buffer (50 mM/pH 7.5). Following addition of 0.5 ml DTT and shaking for 15 minutes at 37° C., the cells were sedimented by centrifugation at 2,500 rpm and washed twice with STM buffer (270 mM sucrose, 10 mM TrisCl, 1 mM $MgCl_2$, pH 7.5). They were then suspended in 0.25 ml STM buffer, and 60 μl aliquots stored at −70° C. For transformation with rDNA integrative vectors, the plasmid DNA was first linearized with XhoI or SacI. 0.1–1 μg of the linearized plasmid DNA was mixed with fresh competent cells defrosted on ice. These preparations were then placed in a 2 mm cuvette. Transformation was performed in a Gene Pulser (Bio-Rad, Munich) at 2.0 kV, 25 μF and 200 Ohm. The cells were then incubated in 1 ml YPD for one hour at 37° C. for recovery before being plated out on selective medium. Macroscopic colonies were visible following incubation for two to four days at 37° C.

Determination of the Glucose Concentration in the Medium

The glucose concentration in the medium was determined by means of the GOD method (GOD/POD Kit, Böhringer).

Samples were diluted 1:200 with water. 190 μl 1% (w/v) GOD enzyme solution (supplied in powder form with the kit) was added to 10 μl of each sample and the mixture was incubated for approximately 25 minutes at 27° C. The glucose solution supplied in the kit was used as the standard, 10 μl (0.91 μg glucose) also being employed here. The absorption was measured in the Anthos 2001 spectrophotometer at 405 nm.

Extraction and Quantitative Detection of Trehalose
Extraction of Trehalose

1–10 ml of cell culture was filtered through a glass-fibre filter (Whatman GF/C) and washed three times with water. The filter was placed in an Eppendorf tube with 1 ml of water and vortexed for 30 seconds before being carefully squeezed out and removed. The cell suspension was then boiled for 10 minutes in the water bath. In order to separate the supernatant completely from the cell material, it was centrifuged three times at 20,000 g.

Determination of Trehalose by HPLC

The extracted sugars were separated by means of a anion exchanger column (DIONEX CarboPac PA1 column, 4×250 mm) and detected amperometrically on a gold electrode (PED=pulsed electrochemical detector). The composition of the eluting gradient is as follows:

| Time (minutes) | H$_2$O | H$_2$O | 1 M Na acetate | 1 M NaCH |
|---|---|---|---|---|
| 0.0 | 45% | 45% | 0% | 10% |
| 3.5 | 40% | 39% | 0% | 21% |
| 4.5 | 35% | 35% | 20% | 10% |
| 5.0 | 45% | 45% | 0% | 10% |
| 14.0 | 45% | 45% | 0% | 10% |

These conditions resulted in a retention time for trehalose of approximately 3.7 minutes. 20 μl of sample was injected in each case. A 0.1 mg/ml trehalose solution was employed as the standard.

Determination of Trehalose by Enzymatic Assay

An equally reliable enzymatic assay method was used in some cases as an alternative to the more expensive HPLC method (Parrou and Francois, 1997, modified): 25 μl of trehalose extract was mixed with 12.5 μl of trehalase (Sigma) and 37.5 μl buffer solution (0.2 M sodium acetate, 0.03 M CaCl$_2$, pH 5.7) and incubated for five hours at 37° C. in a water bath. This resulted in complete breakdown of trehalose to two units of glucose. Following brief centrifugation, the samples were incubated for three minutes at 95° C. and then centrifuged again for a further five minutes at 20,000 g. The trehalose concentration was determined indirectly by determination of the glucose concentration (GOD/POD kit, see above). 10 μl of this supernatant was used for this purpose.

Protein Determination
Protein Determination According to Peterson (Slightly Modified) (Peterson (1997)

In order to determine the total protein concentration of a cell culture 1 ml of cell suspension was precipitated in 1 ml 10% (w/v) TCA and centrifuged for 10 minutes at 3,000 g. The supernatant was drawn by means of a Pasteur pipette connected to a water-jet pump, and the sediment washed in 1 ml 1 N PCA. The pellet was then suspended in 5–12 ml (depending upon the OD of the cell culture to be studied) of a solution of 0.8 N NaOH:10% (w/v) SDS (1:1) and incubated for at least one hour at 60° C. 200 μl of this suspension was added 600 μl 6× dilution of CTC reagent (10% Na$_2$CO$_3$, 0.1% CuSO$_4$.5H$_2$O, 0.2% KNa tartrate). After exactly 10 minutes, 200 μl 6× dilution of Folin-Ciocalteu reagent was added and mixed briefly. The samples were left in the dark for 30 minutes, after which the absorption was measured at 750 nm, BSA serving as the standard.

Protein Determination According to Bradford (1976)

In order to determine the protein concentration in cell-free extract, 100 μl of a suitably diluted extract was mixed with 700 μl of water. 200 μl of BioRad protein assay reagent (Bradford) was then added and briefly shaken (Vortex). The absorption was measured at 595 nm, BSA serving as the standard.

Enzyme Activity Measurements
Preparation of Permeabilized Cells

The enzymatic activity of the trehalose-6-phosphate synthase (Tre-6-P synthase) was measured in permeabilized cells (De Virgilio et al., 1991). For this purpose, 1–6 ml of cells was filtered (on GF/C glass-fibre filters, Whatman), washed twice using ice-cold water, and resuspended by vortexing in 1 ml lyse buffer (0.2 M TRICIN, pH 7.0, 0.5% [v/v] Triton X-100). The filters were removed and the Eppendorf tubes frozen in liquid nitrogen and stored at −20° C. Prior to performance of the measurement, the cells were defrosted in a water bath for three minutes at 30° C. They were then washed twice in 0.2 M TRICIN (pH 7.0), and centrifuged for 20 s at 4° C. and 8,000 rpm (Biofuge 17RS) after each wash. Finally, the cells were resuspended in 600 μl 0.2 M TRICIN (pH 7.0).

Trehalose-6-phosphate Synthase Activity

The Tre6P synthase activity was determined by the coupled enzymatic assay according to Hottiger et al. (1987) at 50° C., 60 μl permeabilized cells always being employed. Both substrate (without glucose-6-P) and enzyme blanks (without permeabilized cells) were processed as controls.

Western Blot Analyses
Protein Extraction by Cell Disruption

5–15 ml of cell culture was centrifuged for 5 minutes at 4° C. and 3,000 rpm (IEC Centra GP8R), and the supernatant then decanted. The pellet was suspended in 1 ml of water and transferred in a Sarstedt tube (with screw closure). Following centrifugation for 10 seconds, the supernatant was drawn by means of a pipette and the pellet weighed, an empty tube serving as a dead weight. 1 μl 0.2 M TRICIN buffer (pH 7.0; with proteinase inhibitors [2 tabs/25 ml]) was added per mg pellet and the pellet resuspended. Glass beads were added until just below the liquid meniscus, after which the Sarstedt tubes were mounted firmly in a cell homogenizer (Fastprep FP120) in the cold store. The cell homogenizer was run twice for 30 seconds at a setting of 6.0, resulting in >90% cell disruption. From this point onwards, strict attention was paid to maintaining the samples well cooled at all times. A small hole was produced in the Sarstedt tube by means of a needle. The tube was placed upon a glass tube and centrifuged at 4° C. and 100 g, thereby separating the extract from the glass beads. The quantity of TRICIN buffer used for cell disruption was then added once to the Sarstedt tubes, which were centrifuged again. The cloudy extract was then transferred to Eppendorf tubes and centrifuged three times for ten minutes at 25,000 g and 4° C. (Biofuge 17RS), the supernatant containing the soluble proteins (including the Tre6P synthase) being subsequently used each time.

Sample Preparation

The protein concentration of these extracts was then determined with the Bradford method (see above). According to the values obtained, they were diluted with water to 2.5 μg protein/μl, and one volume of 5× sample buffer was added to four volumes of this protein solution. The samples were then denatured for five minutes at 95° C. and either used immediately for SDS gel electrophoresis, or frozen. 10 µl, i.e. 20 µg protein, was used for the analysis.

| | |
|---|---|
| Sample buffer: | 1 ml 0.5 M Tris-HCl, pH 6.8, 0.8 ml glycerine, 1.6 ml 10% [w/v] SDS, 0.2 ml 0.05% [w/v] bromophenol blue, 4 ml water.<br>19 volumes sample buffer were added to one volume 2-β-mercaptomethanol immediately prior to use. |

SDS Polyacrylamide Gel Electrophoresis (SDS-PAGE)

The system according to Laemmli et al. (1970) was employed for separation of the proteins according to their molecular weight. A 10% and a 4% acrylamide gel (total dimensions 10×10 cm) with the following composition were prepared for use as the resolving gel and stacking gel respectively:

| | |
|---|---|
| Resolving gel: | 2.5 ml 40% (w/v) acrylamide/bisacrylamide, 2.5 ml 1.5 M Tris-HCl, pH 8.8, 100 µl 10% (w/v) SDS, 4.95 ml water, 50 µl 10% (w/v) ammonium persulphate, 5 µl TEMED |
| Stacking gel: | 1 ml 40% (w/v) acrylamide/bisacrylamide, 2.5 ml 0.5 M Tris-HCl, pH 6,8, 100 µl 10% (w/v) SDS, 6.4 ml water, 50 µl 10% (w/v) ammonium persulphate, 10 µl TEMED |
| 5x running buffer | 15 g Tris, 72 g glycine, 5 g SDS, H$_2$O added to 1 l. The pH value should be approximately 8.3, without further adjustment. |

20 µg of protein was loaded onto each gel. The "Kaleidoscope prestained standard" from BioRad, the composition of which is as follows, was employed as the standard: myosin (204 kDa), β-galactosidase (121 kDa), BSA (78 kDa), carboanhydrase (39 kDa), soy trypsin inhibitor (30 kDa). The gel electrophoresis was performed for approximately one hour (but no longer than for the sample front to reach the lower edge of the gel) at a constant voltage of 200 V. These gels were then either stained with 0.1% (w/v) Coomassie Blue R250 in 10% (v/v) acetic acid/50% (v/v) ethanol (and destained after approximately one hour with 10% (v/v) acetic acid, 20% (v/v) ethanol) or blotted on nitrocellulose (refer to next section).

Immunoblotting

The SDS-PAGE gels were then blotted on nitrocellulose in a blotting unit (Scieplas) with transblot buffer (250 mM Tris, 1250 mM glycine, 15% (v/v) methanol) for 1 hour 15 minutes at 40 V and 40° C.

Immune Staining

The nitrocellulose membrane was first held for at least one hour in a saturation solution comprising 3% (w/v) BSA in TBS (TBS: 20 mM Tris, 500 mM NaCl, pH adjusted to 7.5 with HCl), followed by washing for 5 minutes using TTBS (TTBS: as TBS, but with 0.05% Tween-20). Polyclonal anti-Tps1p rabbit antibody (diluted 1:50 with 1% [w/v] BSA in TTBS) (Eurogentec, Belgium) was then added overnight at 4° C., the purpose of which was to bind to the Tps1 protein (Tps1p) from *H. polymorpha* present on the nitrocellulose.

The nitrocellulose blot was subsequently washed twice for 5 minutes with TTBS and incubated for 1 hour 30 minutes with a monoclonal anti-rabbit antibody coupled with alkaline phosphatase (diluted 1:10.000 with 1% [w/v] BSA in TTBS). This was followed by washing twice for 5 minutes with TTBS and once for 5 minutes with TBS. In order to develop the staining of the bands, 1 ml 10× colour development buffer (100 mM Tris-HCl, pH 9.5, 1 mM MgCl) was diluted 1:10 with water and 45 µl NBT (75 mg/ml 70% [v/v] DMF) and 35 µl X-phosphate (50 mg 5-bromo4-chloro-3-indolyl phosphate, toluidinium salt/ml DMF) were added. The membranes were incubated in the dark with this mixture for 20 minutes (or until the bands became clearly visible) before being washed with water in order to stop the reaction.

Colony PCR with *H. polymorpha* Cells

Colony PCR was performed according to a protocol by Huxley et al. (1990, modified): individual colonies were collected by means of a yellow pipette tip and scraped off in a PCR tube. The tubes were then heated for 2 minutes at full power in a microwave oven. Finally, 25 µl PCR mix (0.2 µl Taq polymerase, 2.5 µl 10× PCR buffer, 2.5 µl 25 mM MgCl$_2$, 0.5 µl 10 mM dNTP, 0.5 µM per final concentration of each primer and water added to bring the volume up to 25 µl) was added to each tube, and the cells resuspended. The tubes were then immediately placed in the PCR unit, which was pre-heated to 92° C., and the program started.

Northern Blot Analysis

RNA was extracted from *H. polymorpha* according to a protocol by Piper (1994, adapted). For this purpose, 40 ml logarithmic or 20 ml stationary cell culture was collected and (in heat shock experiments) cooled immediately by the addition of ice-cold, sterile DEPC water. The cells were then sedimented by centrifugation and washed again with sterile DEPC water. The pellet obtained following centrifugation and discarding of the supernatant was stored at −20° C. Following defrosting, 1–2 g glass beads, 2 ml RNA extraction buffer (20 mM Tris-HCl, pH 8.5, 10 mM Na2-EDTA, 1% [w/v] SDS) and 2 ml phenol were added to the pellet. This mixture was then vortexed without interruption for 5 minutes at room temperature, before being centrifuged for 5 minutes at 3,500 rpm (IEC Centra GP8R). The upper, aqueous phase was transferred to a new tube containing an equal volume of phenol/chloroform (1:1). The suspension was vortexed for 1 minute and centrifuged for 5 minutes at 3,500 rpm, and the supernatant placed in a new tube containing an equal volume of chloroform. Vortexing was repeated for 1 minute, centrifuging at 3,500 rpm for 2 minutes, and the supernatant transferred to 15 ml Corex tubes. 6 M ammonium acetate was added to a final concentration of 1 M ammonium acetate, followed by 2 volumes ethanol (ice-cooled), and the tubes were kept in the freezer compartment at −20° C. for at least 20 minutes. The RNA was then sedimented by centrifugation for 15 minutes at 7,500 g and 40C. The supernatant was decanted and the tubes dried on absorbent paper. The pellets were then suspended in 1 ml TE and the RNA precipitated by the addition of 3 M sodium acetate (to a final concentration of 0.2 M) and 2.5 volumes of ice-cold ethanol. Following centrifugation for 15 minutes at 7,500 g and 4° C., the pellet was washed with ice-cold 70% (v/v) ethanol and dried at room temperature. Finally, the RNA was resuspended in 400 µl TE.

Sample Preparation

50 µg RNA per sample was dried in the SpeedVac for 10–15 minutes for the Northern blot analysis (according to Sambrook et al., 1989). The RNA was then resuspended in 50 µl sample buffer (final concentrations: 20 mM MOPS, pH 7.0, 0.5 mM sodium acetate, 1 mM EDTA, pH 8.0, 2.2 M formaldehyde, 50% [v/v] formamide) and heated for 10 minutes at 55° C. Finally, 5.5 µl RNA loading buffer (10×) and 1 µl ethidium bromide solution (1 µl/ml) were added to each sample.

Pre-Gel and Main Gel

A pre-gel (1% [w/v] agarose and 0.65 M formaldehyde in a MOPS buffer containing 40 mM MOPS, pH 7.0, 10 mM sodium acetate, 2 mM EDTA, pH 8.0) was used to test the integrity of the extracted RNA and to calibrate visually the loaded quantity. The main gel electrophoresis (composition identical to that of the pre-gel) was performed for 34 hours at 80 V with MOPS buffer serving as the running buffer.

Blotting

The gels were first washed twice for 20 minutes in 10×SSC (1.5 M NaCl, 170 mM sodium citrate). The RNA was then blotted overnight by capillary transfer (with 20×SSC as the transfer buffer) onto a nitrocellulose membrane (BA 83). The membrane was then washed in 6×SSC, placed between 3 MM filter papers (Whatman) and baked in a vacuum oven for 2 hours at 80° C., which enabled the RNA to be fixed to the nitrocellulose.

Hybridization

The nitrocellulose membrane was pre-hybridized in a special oven (Hybaid) in 10 ml RNA hybridization solution (0.5 M $NaHPO_4$, pH 7.2, 1 mM EDTA, 1% [w/v] BSA, 7% [w/v] SDS) for 5 hours at 60° C. For the main hybridization stage, 150 µl of the radioactive probe (approximately $1\times10^7$ cpm in total) was added to 10 ml RNA hybridization solution and the membrane incubated in it overnight at 60° C. Finally, the surplus radioactivity was washed twice for 15 minutes at 60° C. with 300 ml washing buffer (1 mM EDTA, 40 mM $Na_2HPO_4$, pH 7.2, 1% [w/v] SDS). The nitrocellulose membrane was exposed on BioMax film.

Phytase Detection

The *H. polymorpha* cells were harvested from 3 ml overnight cultures and suspended in 200 µl YNB medium and 1 ml 5% glycerine. Following growth over 1–2 days, the $OD_{600}$ was first determined. The cells were then sedimented by centrifugation and 25 µl of the supernatant was subsequently used. 25 µl 5 M NaAc and 50 µl 4-nitrophenyl phosphate were added to this aliquot. The mixture was incubated for 30 minutes at 37° C. The enzymatic conversion of the substrate was halted by the addition of 100 µl 15% trichloroacetic acid. Following the addition of 100 µl 1 M NaOH, supernatant samples of positive cultures were deep yellow coloured. The yellow colour was quantified by $OD_{405}$ measurement in the photometer.

X-gal Overlay Assay—Detection of β-galactosidase

The strains to be tested were cultivated in selective medium for 4–6 hours at 37° C. A 4 µl drop of each culture was placed on a selective plate and incubated overnight at 37° C. The plate was coated with fresh top layer agar (0.5% agarose, 0.5 M $Na_2HPO_4/NaH_2PO_4$ (pH 7); 0.2% SDS; 2% DMF (dimethyl formamide) 2 mg/ml X-gal (o-nitrophenyl-β-D-galactopyranoside) at 70° C. After a few minutes, the clones with lacZ expression exhibited blueness.

Example 1

Cloning of the TPS1 Gene of *H. polymorpha*

Preparation of a Radioactive TPS1 Probe

Based upon a sequence comparison of the known TPS1 genes of *S. cerevisiae, S. pombe, K. lactis, Candida albicans* and *A. niger* (see FIG. 6), two degenerated primers could be prepared from two highly conserved regions which amplified a fragment of approximately 650 bp during PCR (consisting of 30 cycles each comprising 1 minute at 92° C., 30 seconds at 52° C., 1 minute at 72° C.) with genomic DNA from *H. polymorpha*. The sequences of the two primers were as follows:

```
                                                (SEQ ID NO:9)
F1 (forwards):    5' TGGCCVYTNTTCCAYTACCATCGYGG 3'

(SEQ ID NO:10)
R1 (backwards):   5' GGCRTGBAAYTTYTGHGGHACACC 3'

B = C, G, T       H = A, C, T      R = A, G
    V = A, C, G       N = A, C, G, T   Y = C, T
```

The PCR product was then loaded onto a preparative 1% (w/v) agarose gel and separated electrophoretically. The 650 bp band was cut out, extracted using the Geneclean II kit (Bio 101, Vista, USA), and marked with radioactive [α-$^{32}$P]-dCTP. The Prime-It II kit was employed for this purpose, and the NucTrap columns for cleaning. This radioactive probe was used for the TPS1 screen of *H. polymorpha* and for the Northern blot analysis.

Genomic DNA Library of *H. polymorpha*:

The genomic DNA library used was made available by R. Hilbrands (University of Groningen, Netherlands). Preparation of the genomic DNA library is not critical, provided the fragments are ≧ approximately 2 kb. Genomic DNA fragments of *H. polymorpha* 2–5 kb in length (possibly several times this length) were cloned into the BamHI restriction site of pHRP2 (7813 bp). This plasmid (Faber et al., 1992) contains an ori (replication origin) and an ampicillin-resistance gene for replication and selection in *E. coli*. For transformation of *H. polymorpha* the HARS1 sequence (*H. polymorpha* autonomously replicating sequence) and the *S. cerevisiae* LEU2 gene acting as a marker which also functions in *H. polymorpha* are present. This library contains some 20,000 different clones.

Transformation of *E. coli*

Transformation of *E. coli* with the genomic DNA library was performed by electroporation (Sambrook et al., 1989) and cells were plated out onto 50 LB+Amp (75 mg/l) plates (2,000–4,000 colonies per plate). The plates were incubated overnight at 37° C.

Screening for the TPS1 Gene of *H. polymorpha*

In order to permit analysis of the DNA of the individual colonies, nitrocellulose membranes were carefully placed on the plates (according to Sambrook et al., 1989). A thin needle was used to produce four asymmetrically distributed holes through the membrane and gel. These acted as markers in order to enable the orientation of the membranes on the plates to be reproduced at a later stage. When the membranes were drawn, the colonies present on the plate were replicated.

Four plastic dishes containing 3 MM absorbent paper (Whatman) were then laid out, and each dish moistened with one of four different solutions. Surplus liquid was discarded. The nitrocellulose membranes were first placed (with the colonies facing upwards) on absorbent paper soaked in 10% (w/v) SDS for 3 minutes. They were then placed in the second dish containing denaturing solution (0.5 N NaOH, 1.5 M NaCl) and held there for 5 minutes. Then they were held in turn on absorbent paper with neutralizing solution (1.5 M NaCl, 0.5M Tris-HCl, pH 7.4) and with 2×SSC (10×SSC 1.5 M NaCl, 170 mM sodium citrate), for 5 minutes each. In order to fix the DNA to the nitrocellulose, each membrane was placed between two 3 MM absorbent papers and baked in a vacuum oven at 80° C. for 2 hours. The membranes were then moistened for 5 minutes in 2×SSC, before being dipped for 30 minutes in a prewash solution at 50° C. (5×SSC, 0.5% [w/v] SDS, 1 mM EDTA, pH 8.0). A wet Kleenex was used to wipe away surplus bacterial material before the membranes were placed for 2 hours in pre-hybridization solution (6×SSC, 0.25% [w/v]

skim-milk powder) at 68° C. For the main hybridization process, approximately 1×10⁷ cpm of radioactive TPS1 probe (refer to "preparation of a radioactive TPS1 probe") was placed in 40 ml pre-hybridization solution, and the membranes incubated in it overnight at 68° C. Following brief rinsing three times in 2×SSC, 0.1% (w/v) SDS and washing for 1 hour at 68° C. in 1×SSC, 0.1% (w/v) SDS, the membranes were dried and exposed on BioMax film. The signals on the developed films enabled 8 positive colonies to be picked on the plates and stocks created from them. The plasmids were extracted from these colonies. PCR was employed to test whether the 650 bp fragment was in fact present.

Example 2

Sequencing of the TPS1 Gene of *H. polymorpha*

Plasmid Isolation

For sequencing, two colonies were selected which, by means of PCR with primers from within the 650 bp fragment outwards (F4 and R4, see Table 1) and from the plasmid towards the insert (Plasm. F and Plasm. R, see Table 1) yielded the largest possible bands. Pure plasmid extracts were prepared from these colonies (Nos. 20.1 and 21.3) by means of the Plasmid Midi Kit (Qiagen).

Sequencing

Sequences were produced by means of a cyclical sequencing program (PCR apparatus: Progene) and the ABI 301 automatic sequencer (Perkin Elmer). 0.5 µl (0.5 µg) plasmid DNA, 1 µl primer (final concentration 0.5 µM), 4 µl reaction mixture (DNA sequencing kit) and 4 µl water were used for this purpose. The sequencing program employed involved 27 cycles comprising 30 seconds at 96° C., 15 seconds at 50° C., and 4 minutes at 60° C. Upon completion of the program, 10 µl water was added to the reaction, and the DNA precipitated with sodium acetate and ethanol. The pellet was washed twice using 1 ml ice-cold 70% (v/v) ethanol. The DNA was then dried briefly and resuspended in 25 µl TSR (template suppressing reagent, DNA Sequencing Kit). Following incubation for two minutes, the samples were then ready for sequencing in the ABI 301.

The primers employed for sequencing the plasmid from clone No. 21.3 are listed in Table 1. They were prepared at the FMI on "Expedite™ Nucleic Acid Synthesis" equipment. The sequences were analyzed by means of the GCG program (Devereux et al., 1984).

TABLE 1

List of primers employed for sequencing the TPS1 gene

| Name | Direction | Length (bp) | Sequence | |
|---|---|---|---|---|
| F3 | Forwards | 23 | 5' GGAAGCAAATAAACTGTTTTGCC 3' | (SEQ ID NO:11) |
| F4 | Forwards | 23 | 5' CTGTAAGTGCTTATCCGATTGGC 3' | (SEQ ID NO:12) |
| F6 | Forwards | 22 | 5' GGACGACAAACTGTCGAGCGGG 3' | (SEQ ID NO:13) |
| F7 | Forwards | 22 | 5' CATACTCCTTTTCCTTCAAGCG 3' | (SEQ ID NO:14) |
| F8 | Forwards | 21 | 5' AAAGCGTGAACTTCCAAGAGC 3' | (SEQ ID NO:15) |
| F9 | Forwards | 22 | 5' GCGTGTGATTACTGTGGTTTGC 3' | (SEQ ID NO:16) |
| F10 | Forwards | 26 | 5' GGTGAGATAATATTTTCGAAATTTCC 3' | (SEQ ID NO:17) |
| F11 | Forwards | 27 | 5' CCCATCAAATGCAGCAAGATATTGACC 3' | (SEQ ID NO:18) |
| R3 | Backwards | 21 | 5' CCATTCAAGAATTTGTCAACG 3' | (SEQ ID NO:19) |
| R4 | Backwards | 23 | 5' CATGAGATGATAATCATGTACCC 3' | (SEQ ID NO:20) |
| R5 | Backwards | 23 | 5' CAATTTTGACATTCGGTAGCCCC 3' | (SEQ ID NO:21) |
| R6 | Backwards | 22 | 5' GTAATGCCGTCACTAATCCGCC 3' | (SEQ ID NO:22) |
| R7 | Backwards | 23 | 5' GAACATCTTCTGAAAATTGCCCC 3' | (SEQ ID NO:23) |
| R8 | Backwards | 21 | 5' CTAGCTCATTTACAGCTGCCC 3' | (SEQ ID NO:24) |
| R9 | Backwards | 25 | 5' CATAGCTTTCGAGCCTTTCATCTGG 3' | (SEQ ID NO:25) |
| Plasm F | Forwards | 24 | 5' GGCGAGCCCGATCTTCCCCATCGG 3' | (SEQ ID NO:26) |
| Plasm R | Backwards | 26 | 5' CTGCTCGCTTCGCTACTTGGAGCCAC 3' | (SEQ ID NO:27) |

Figure 3A:
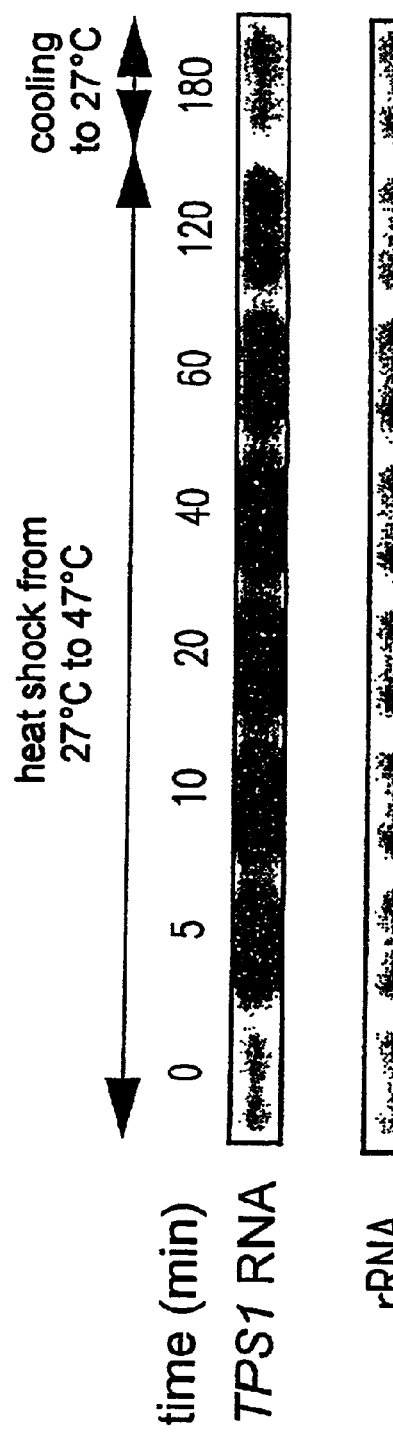
FIG. 3A shows a Northern blot of RNA from wild-type *H. polymorpha* following a heat shock from 27° C. to 47° C. and subsequent cooling to 27° C. The cells were cultivated in YDP medium at 27° C. to the early exponential phase; the temperature was then increased to 47° C. (time zero), and reduced again to 27° C. after 120 minutes.
Figure 3B:
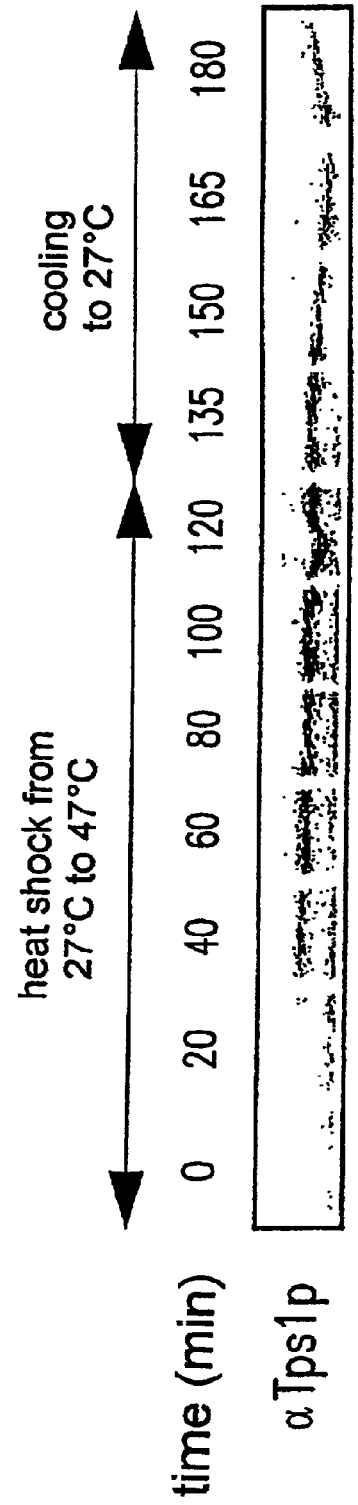
FIG. 3B shows a Western blot for the Tps1 protein (Tps1 p) from *H. polymorpha* following a heat shock from 27° C. to 47° C. and subsequent cooling to 27° C. (see FIG. 3A), from which a correlation can be seen between in the increase of TPS1 mRNA and the increase in Tps1 protein (Tps1p).
Figure 3C:
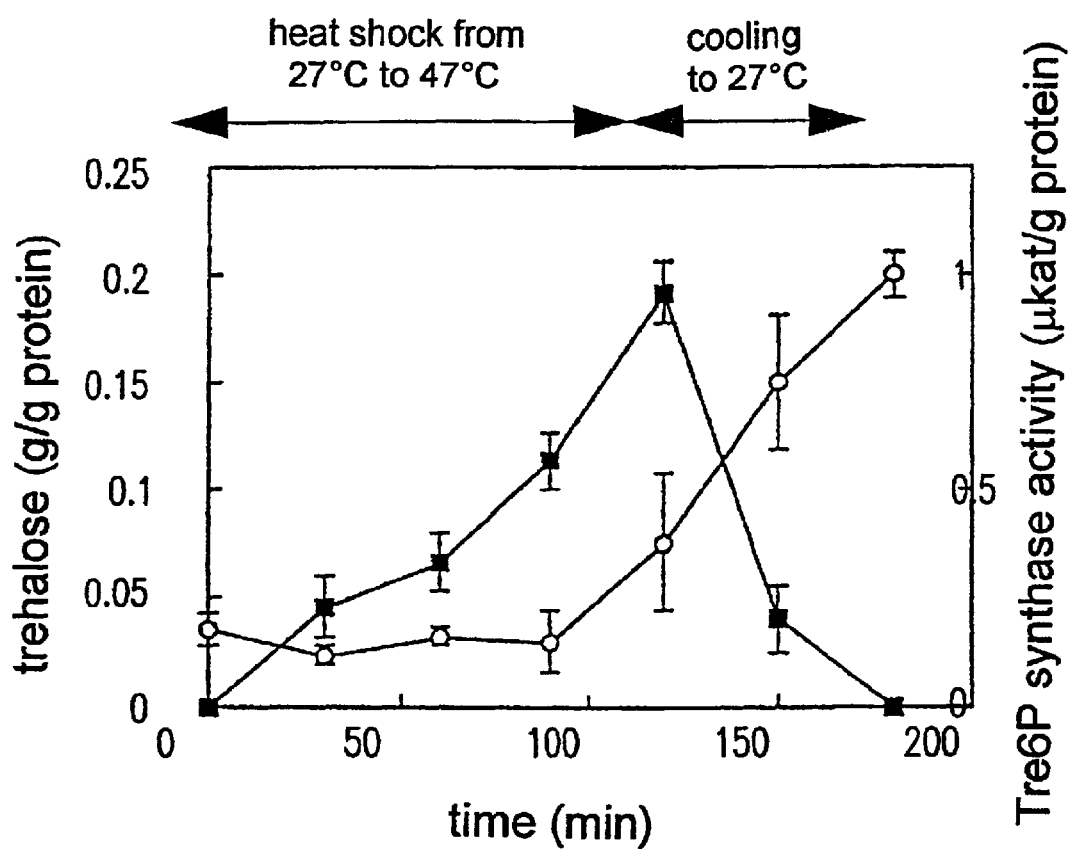
FIG. 3C shows the intracellular trehalose concentration and the trehalose-6-phosphate synthase activity plotted against time for *H. polymorpha* following a heat shock from 27° C. to 47° C. and subsequent cooling to 27° C. (see FIG. 3A). The open circles represent the intracellular trehalose concentration, the solid squares the trehalose-6-phosphate synthase activity. A correlation is evident from the figure between the increase in TPS1 mRNA, and the increase in trehalose-6-phosphate synthase activity and the intracellular trehalose concentration.

A promoter isolated from *H. polymorpha* and its mode of action are described in greater detail below. This promoter, which controls the expression of TPS1, was studied by measurement of the increase in TPS1 mRNA under certain conditions. It was found that whilst this promoter expressed small quantities of TPS1 at temperatures very low for *H. polymorpha*, the expression increased very strongly at high temperatures, i.e. much more strongly than is the case with heat shock-induced promoters previously described (see FIG. 3A, Northern blot of the heat shock). The heat-induced increase in TPS1 mRNA correlates with the increase in Tps1 protein (FIG. 3B), with the increase in trehalose-6-phosphate synthase activity, and with the increase in the intracellular trehalose concentration (FIG. 3C). In order to optimize the thermal influence, the promoter can for example be selectively shortened and coupled with further segments containing HSE.

Figure 4A:
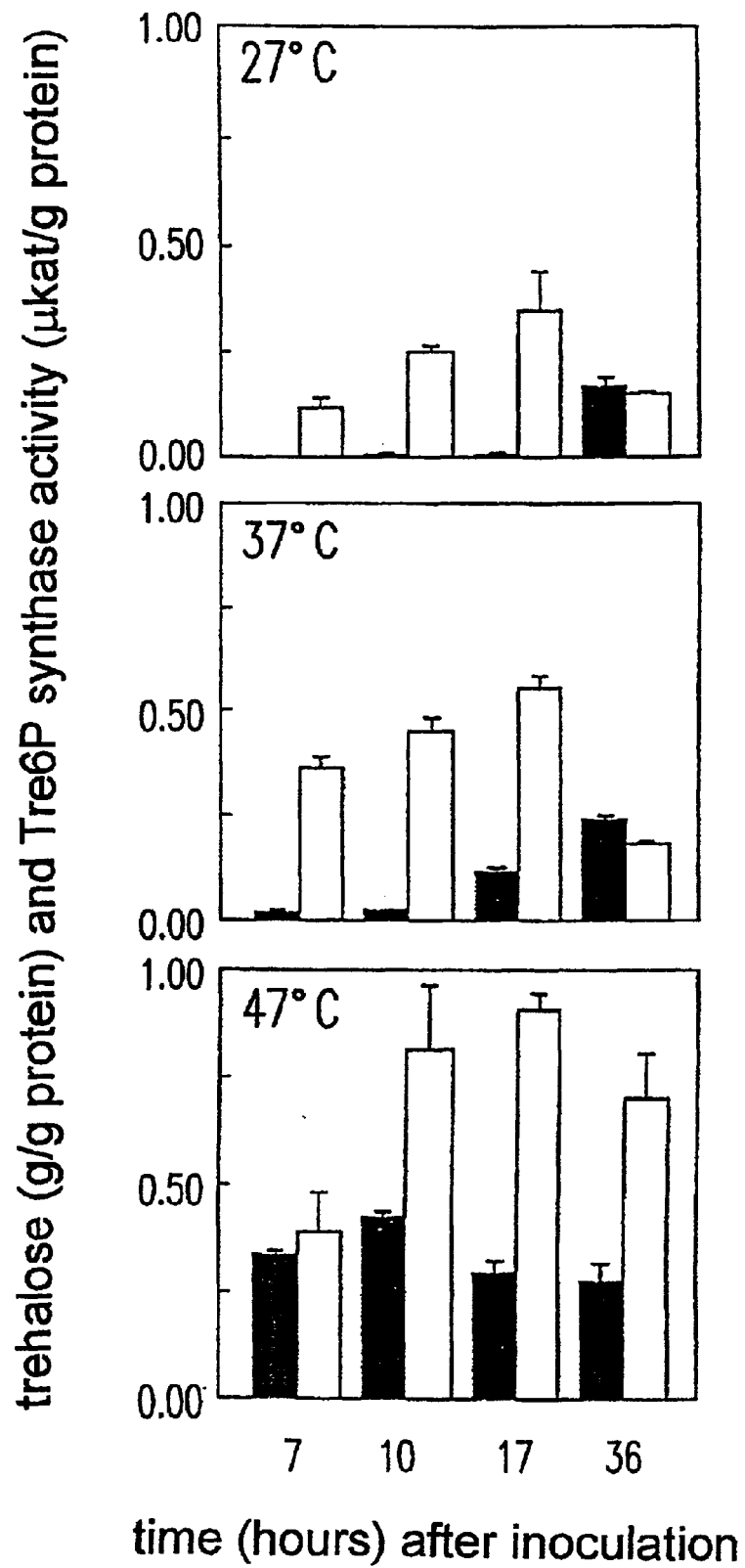
FIG. 4 shows three bar charts representing the trehalose-6-phosphate synthase activity (white bars) and the intracellular trehalose concentration (black bars) in cells of *Hansenula polymorpha* cultivated at 27° C. (A), 37° C. (B) and 47° C. (C) and under glucose deprivation after 7, 10, 17 and 36 hours. The trehalose accumulation correlates to the increase in trehalose-6-phosphate synthase activity (FIG. 4A), to that of the TPS1 mRNA (FIG. 4B) and to that of the Tps1 protein (Tps1p) (FIG. 4C).
Figure 4B:
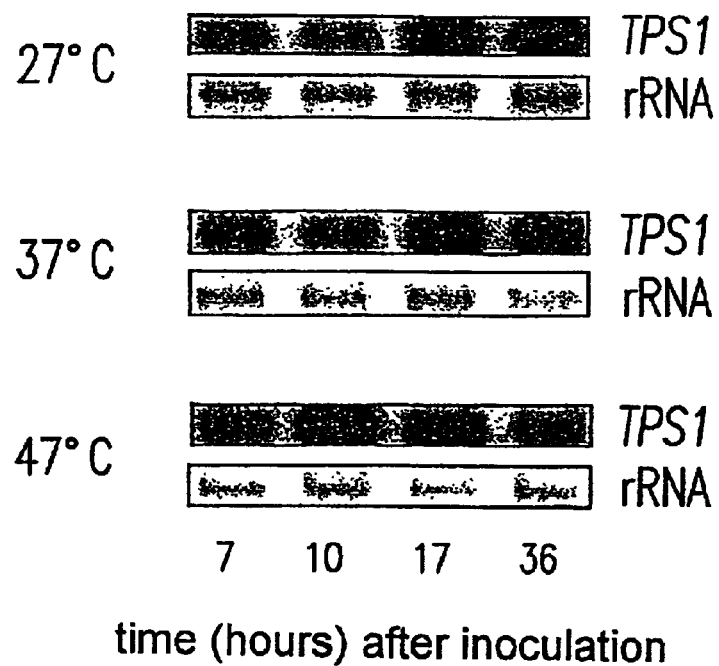
Figure 4C:
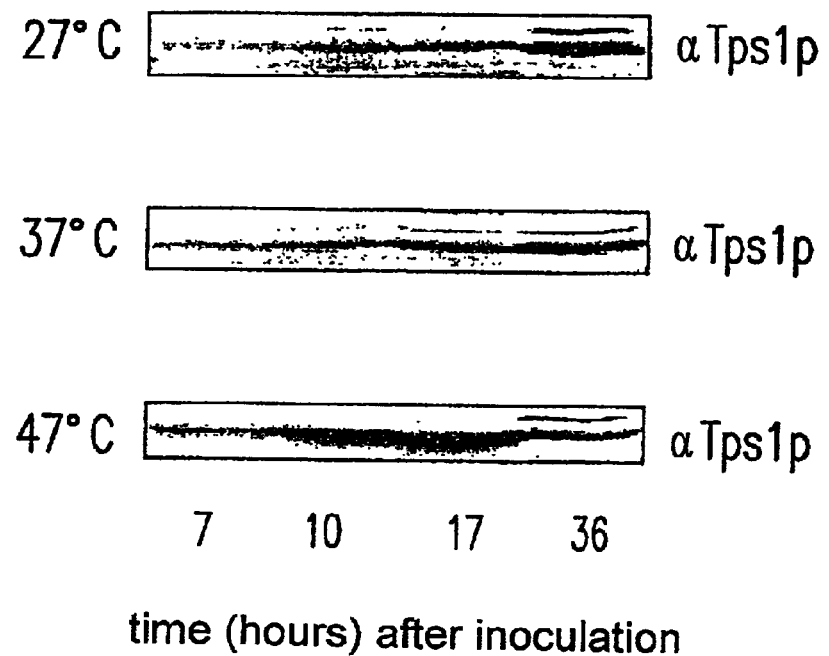

In addition to heat induction, a trehalose accumulation dependent upon the glucose deprivation was also observed, as anticipated owing to the close biological relationship between these two stress factors (see FIG. 4A). This trehalose accumulation correlates with the increase in trehalose-6-phosphate synthase activity, the increase in TPS1 mRNA (FIG. 4B), and the increase in trehalose accumulation observed with the increase in Tps1 protein during glucose deprivation (FIG. 4C).

The extremely high accumulation of TPS1 mRNA indicates that the TPS1 mRNA is highly stable, which makes it (and the cDNA based upon it or information obtainable from it) not only a valuable tool for isolation of the promoter, but also a particularly valuable means for protecting other organisms against a range of stress conditions, such as heat or drought. TPS1 DNA provided with suitable promoters and vectors (for example as described in WO 93/17093 and WO 96/00789) can for example be employed to protect plants against water deprivation, thus enabling them to be cultivated in warmer regions and regions with lower precipitation. Not only TPS1 DNA, but also DNA related to it can of course also be employed for this purpose.

Example 3

Figure 7:
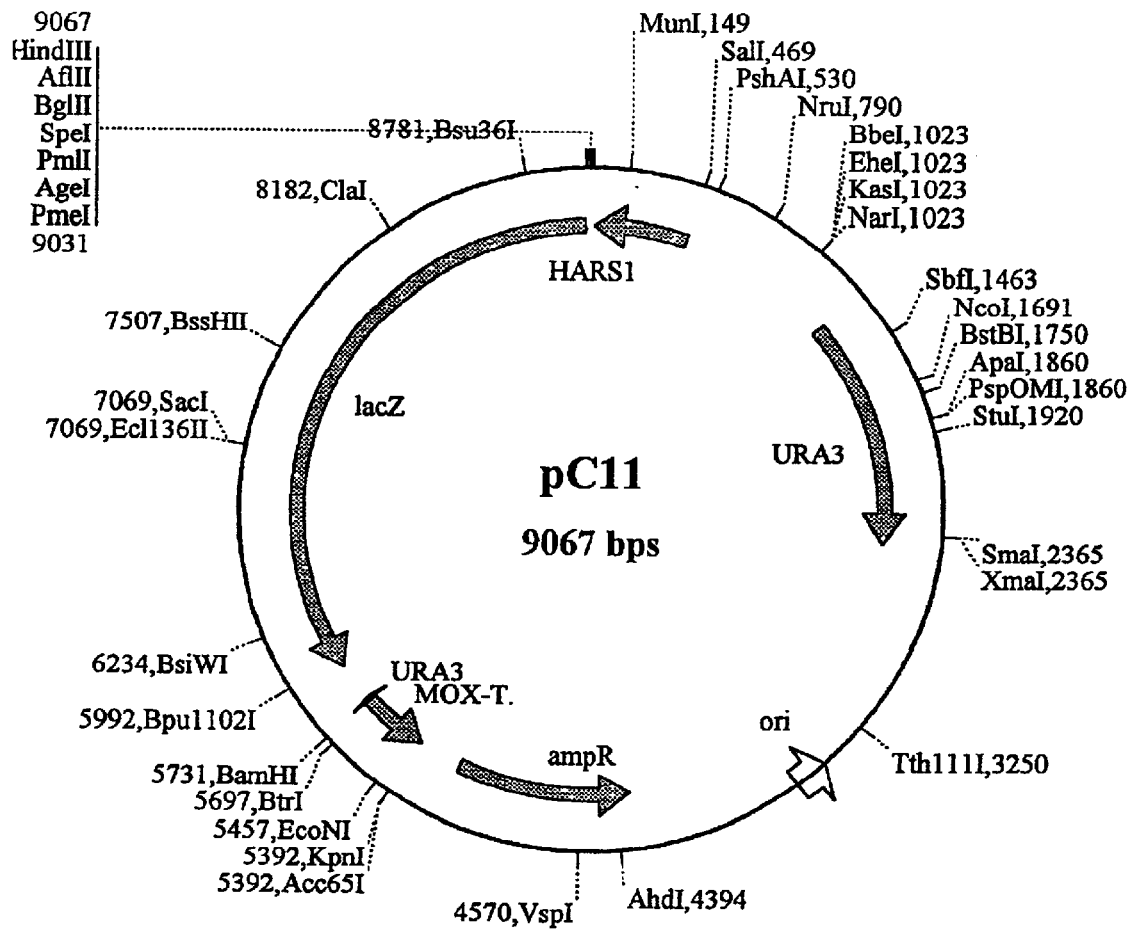
FIG. 7 shows the plasmid pC11, a derivative of pM1 (M. Suckow, personal communication), which was obtained by insertion of the lacZ gene into the polylinker of pM1. The plasmid contains the HARS1 sequence (*H. polymorpha* Autonomously Replicating Sequences), the ori (origin of replication) from pBR322, an ampicillin-resistance gene, the URA3 gene for propagation and selection in *H. polymorpha* and in *E. coli*, and a MOX terminator behind the lacZ gene for termination of the transcription process.
Figure 8:
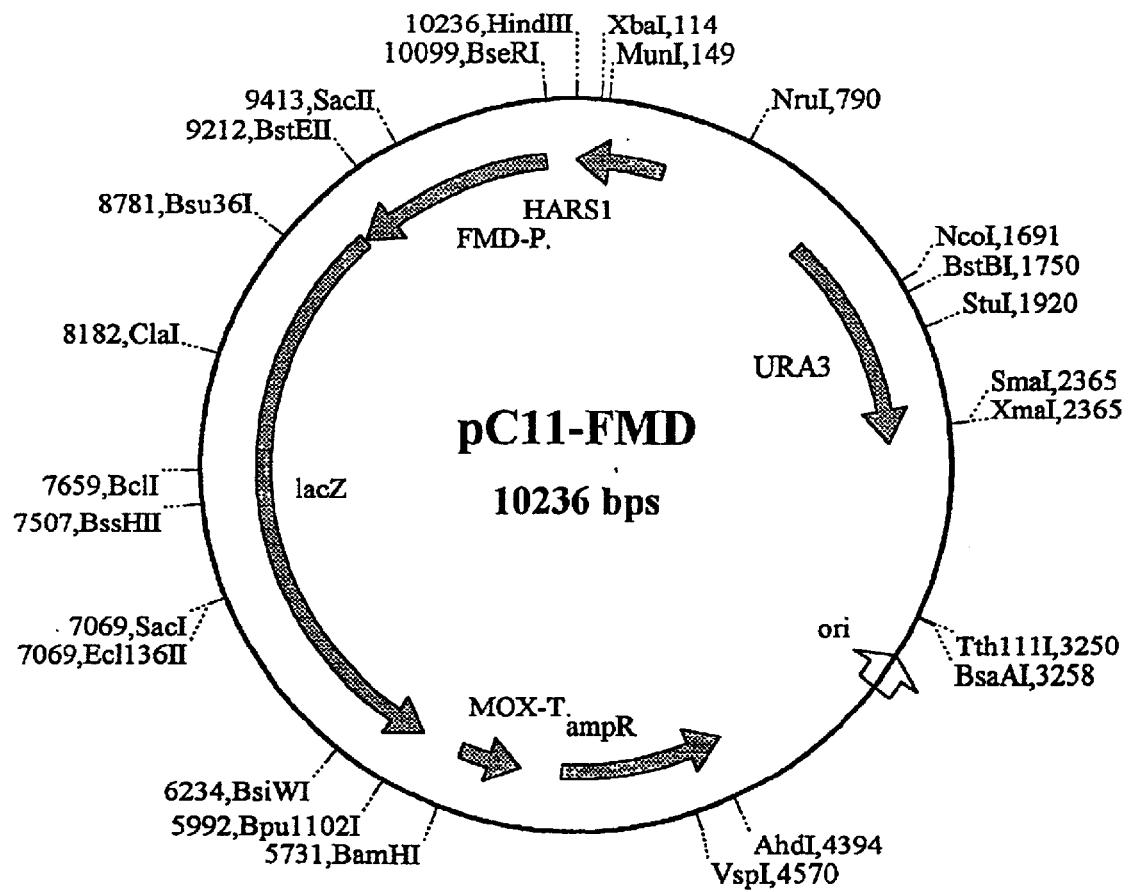
FIG. 8 shows the plasmid pC11-FMD obtained by insertion of the FMD promoter in front of the lacZ reporter gene of pC11.
Figure 9:
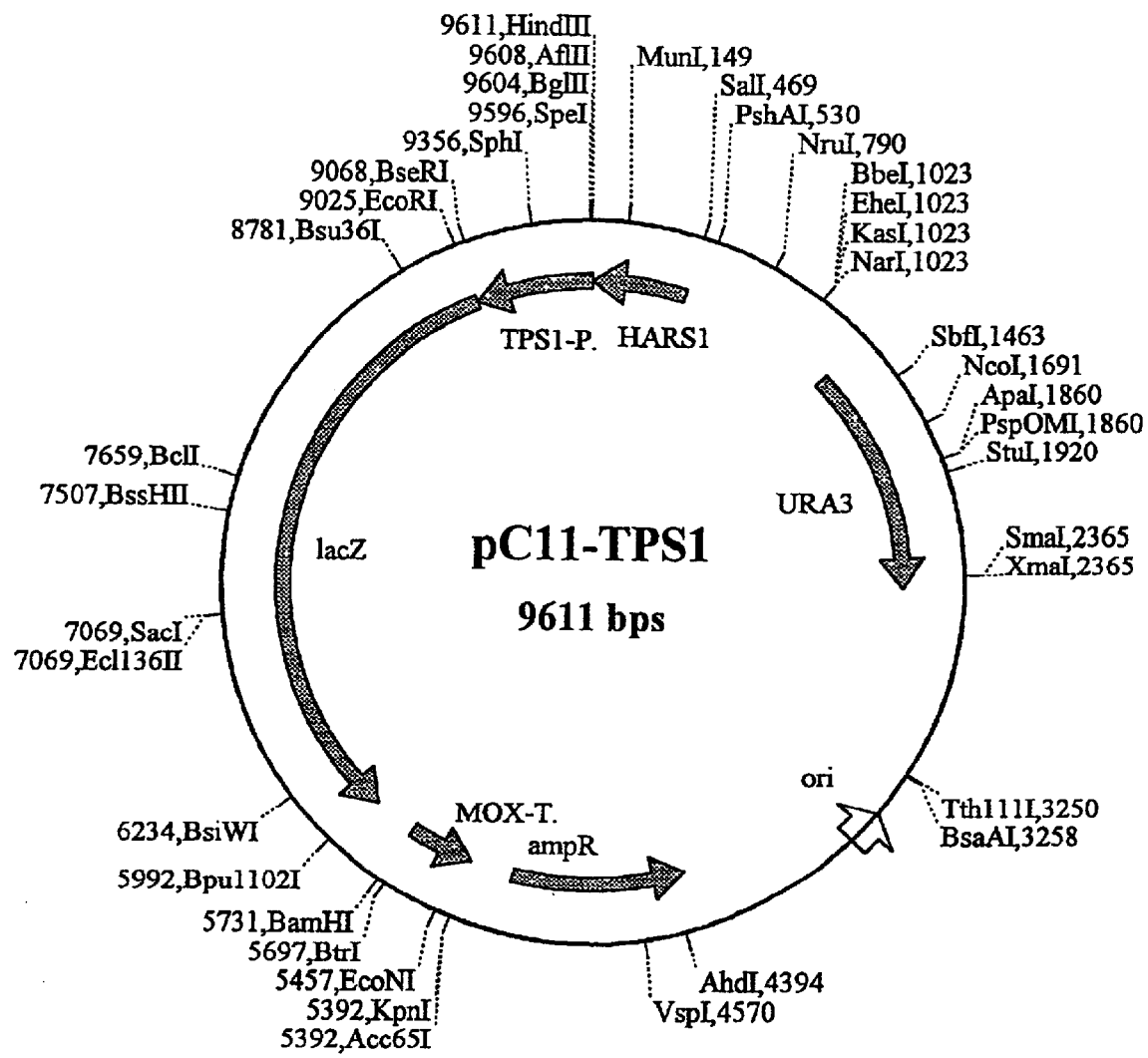
FIG. 9 shows the plasmid pC11-TPS1 obtained by insertion of the TPS1 promoter in front of the lacZ reporter gene of pC11.

Comparative Expression of a Bacterial lacZ Gene Under the Control of the FMD and the TPS1 Promoter Based upon the integrative *H. polymorpha* vector pC11 (FIG. 7), two derivatives were constructed which differ only in the respective promoter in front of the lacZ reporter gene. In the case of pC11-FMD (FIG. 8), the lacZ gene is under the control of the FMD promoter, which has already been well characterized. In the case of pC11-TPS1 (FIG. 9), it is under control of the heat-inducible promoter to be tested. For the purpose of this experiment, the fragment between nucleotides 228 and 792 of the sequence indicated under SEQ ID NO:1 (referred to below as the TPS1 promoter) was used as the heat-inducible promoter.

*H. polymorpha* RB11 was transformed with pC11-FMD and pC11-TPS1 (refer to Materials and Methods). Stable strains in which the respective plasmid was present in a genomically stable integrated state were produced separately from approximately 1,000 uracil-prototrophic cell clones for each transformation. The procedure in this case was as follows: following transformation, the cells were plated out onto plates containing selective media. Macroscopic discrete colonies were visible after three days. In both cases, 1,000 discrete separate colonies were transferred under sterile conditions to new selective plates, which were then incubated for two days at 37° C. This procedure was repeated a further two times (passaging). The cell clones were then transferred to full medium plates and incubated again for two days at 37° C. (stabilization). Finally, the cell clones were transferred again to selective plates, in order to eliminate any remaining free plasmids. Following incubation of these plates for two days at 37° C., production of the strains was complete. The exact number of copies and the integration loci of the plasmids in the individual strains were not determined; according to Gatzke et al. (1995), however, the various strains produced should differ clearly from each other in this respect.

Since both the copy number and the genomic environment have a major influence upon the transcription rate of a gene, it had to be assumed that the individual cell clones would also differ considerably from each other with regard to their β-galactosidase activity. This was experimentally confirmed (data not shown). It was not therefore possible to compare promoter strengths directly by means of individual strains. To permit objective promoter studies despite this, 500 individual strains which had been produced separately were combined, the objective being to create representative strain mixtures with regard to the copy number and integration loci. Since the plasmids pC11-FMD and pC11-TPS1 used for strain production are identical with the exception of the respective promoter located in front of the lacZ gene, it can be assumed that they are integrated into the host genome in a homologous manner. This assumption was confirmed by the observation that various strain mixtures from the same transformation differ from each other only slightly in their β-galactosidase activity (data not shown). Determination of the β-galactosidase activity of strain mixtures produced by transformation with plasmids which are largely identical should therefore permit objective promoter comparisons in *H. polymorpha*.

Figure 10A:
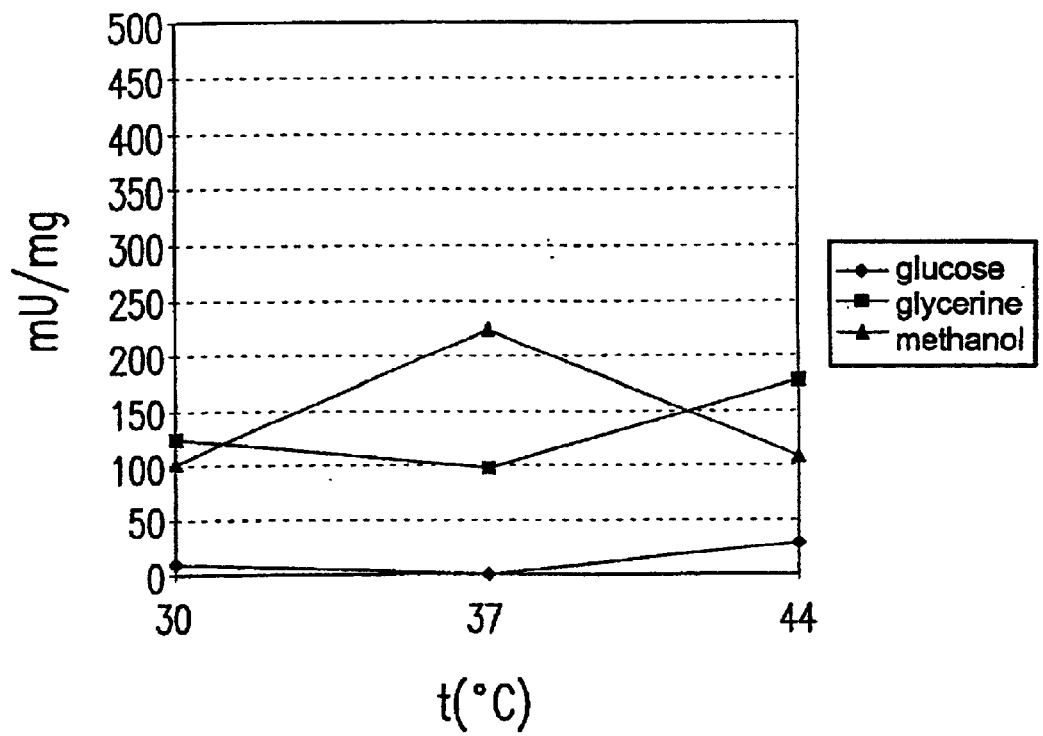
FIG. 10 shows a comparison between the activity of FMD (A) and TPS1 promoters (B) at 30, 37 and 44° C. in three different carbon sources (2% glucose, 2% glycerine or 2% methanol).
Figure 10B:
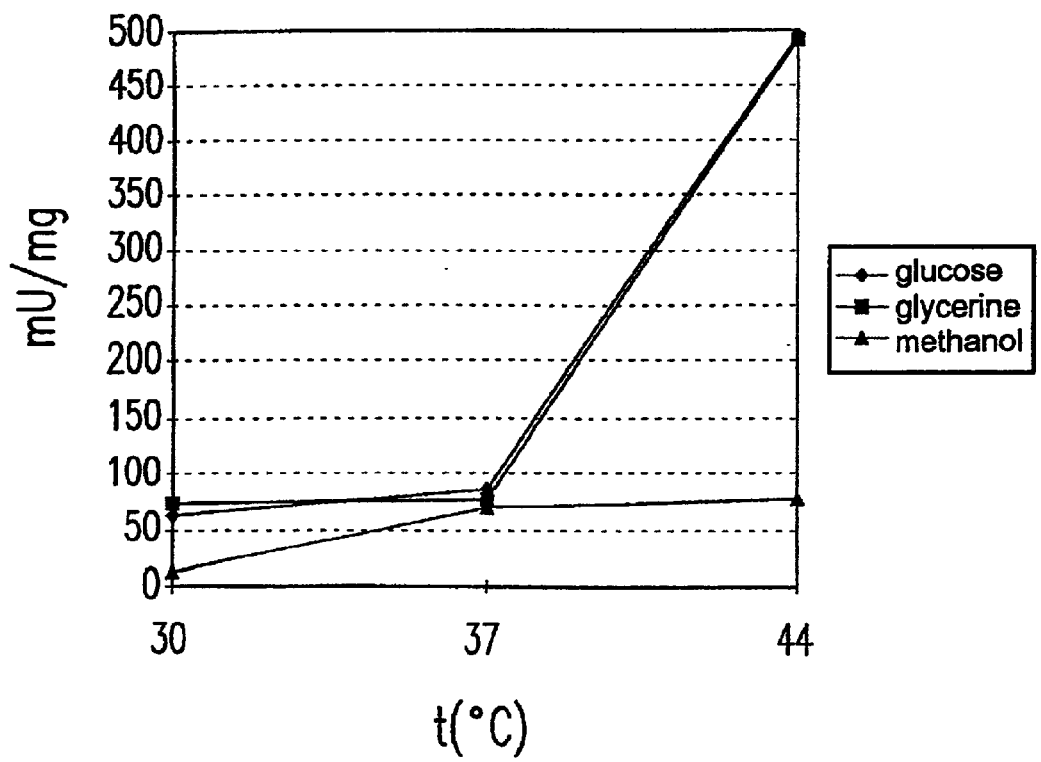

The lacZ activities under the control of FMD or TPS1 promoters were performed at three different temperatures in three different carbon sources (see FIG. 10). To this end, the strain mixtures described above were cultivated to an $OD_{600}$ of 5 in 10 ml selective medium at the temperatures and with the carbon sources indicated, after which cell extracts were prepared, the β-galactosidase activities of which were determined by means of ONPG measurements in liquid media. The procedure was as follows: upon attainment of the desired density, the cultures were centrifuged for 10 minutes at 4° C., the cell pellets washed in 10 ml lacZ buffer (50 mM sodium phosphate buffer, pH 7; 10 mM KCl; 1 mM $MgSO_4$), resuspended in 500 µl lacZ buffer, and transferred to 1.5 ml Eppendorf tubes. Glass beads 0.45 mm in diameter were added to the suspensions (up to the meniscus of the liquid), after which the cells were disrupted in a Vibrax (Janke & Kunkel; 6 minutes; 4° C.; 2,200 rpm). The cell lysates were removed and centrifuged (bench centrifuge; 4° C.; 10 minutes). The soluble fractions were used both for determination of the β-galactosidase activities and for measurement of the total protein content. For the β-galactosidase activity measurements, 1 ml ONPG solution (4 mg ONPG/ml lacZ buffer) was added to various dilutions of the soluble fractions, and each mixture was then transferred to a 1 cm plastic cuvette. The $OD_{420}$ was then measured at 30-second intervals over a period of 3 minutes in order to permit measurement of the ΔE. To determine the total protein content of the cell extracts, 790 µl $H_2O$ was mixed with 10 µl of the respective soluble fraction (diluted 1:10, 1:5, 1:2 or undiluted, according to the protein content) and 200 µl Bradford reagent (Biorad) was added. Following incubation for 10 minutes at room temperature, the $OD_{490}$ was determined photometrically and adjusted to a control sample containing lacZ buffer instead of cell extract. The protein concentration in the cell extract was then determined from the absorption values by means of a BSA calibration curve. The specific β-galactosidase activities were calculated according to the following formula:

Volume activity $(mU/mL) = \Delta E/Ved \ v$ total proteins

V: total volume
v: sample volume
e: extinction coefficient (0.0045 mM cm)
d: layer density (1 cm)

Following transformation by electroporation, recombinant *H. polymorpha* strains were obtained by growing the uracil-prototrophic clones produced by transformation on selective medium over at least 80 generations (Gatzke et a., 1995). Representative transformants of the two strain collections produced were cultivated comparatively under different conditions in 3 ml liquid cultures. Cultivation was performed in a YNB medium buffered with 0.1 M phosphate buffer pH 5.0 supplemented with 2% glucose or 5% glycerine. After 48 hours the secreted phytase was quantified in the aliquots of the culture supernatant with the aid of the method described under Materials and Methods.

|  | FMD Conphys | | | TPS1Conphys | | | |
|---|---|---|---|---|---|---|---|
| Temperature | mg/L | $OD_{600}$ | mg/OD | mg/L | $OD_{600}$ | mg/OD | |
| 37° C. | 2.185 | 1.453 | 1.500 | 2.026 | 1.104 | 1.840 | Glycerine |
|  |  |  |  | 2.028 | 0.626 | 3.240 | Glucose |
| 40° C. | 0.916 | 0.618 | 1.480 | 1.336 | 0.697 | 1.920 | Glycerine |
|  |  |  |  | 2.379 | 0.448 | 5.300 | Glucose |
| 44° C. | 0.706 | 0.774 | 0.910 | 1.219 | 0.671 | 1.820 | Glycerine |
|  |  |  |  | 1.394 | 0.418 | 3.330 | Glucose |

The FMD promoter is known to be controlled primarily by the type of the carbon source; a temperature dependency has not yet been described (EP Patent No. 299108). This was confirmed by the measurements performed here (see FIG. 10A). The β-galactosidase activities were shown to be low under glucose conditions (glucose repression), whereas substantially higher values were measured under glycerine or methanol conditions (derepression or induction). Temperature changes did not lead to dramatic changes in the measured values obtained (see FIG. 10A). This was also observed in the test system employed here. The β-galactosidase activities were low at 30° C. or 37° C., but rose dramatically at 44° C. (see FIG. 10B). This temperature-dependent rise in promoter activity did not occur under methanol conditions (FIG. 10B), a phenomenon which has not yet been described. Surprisingly, the highest β-galactosidase activities measured for TPS1 promoters were substantially higher than those for FMD promoters (see FIGS. 10A, B).

Example 4

Figure 11:
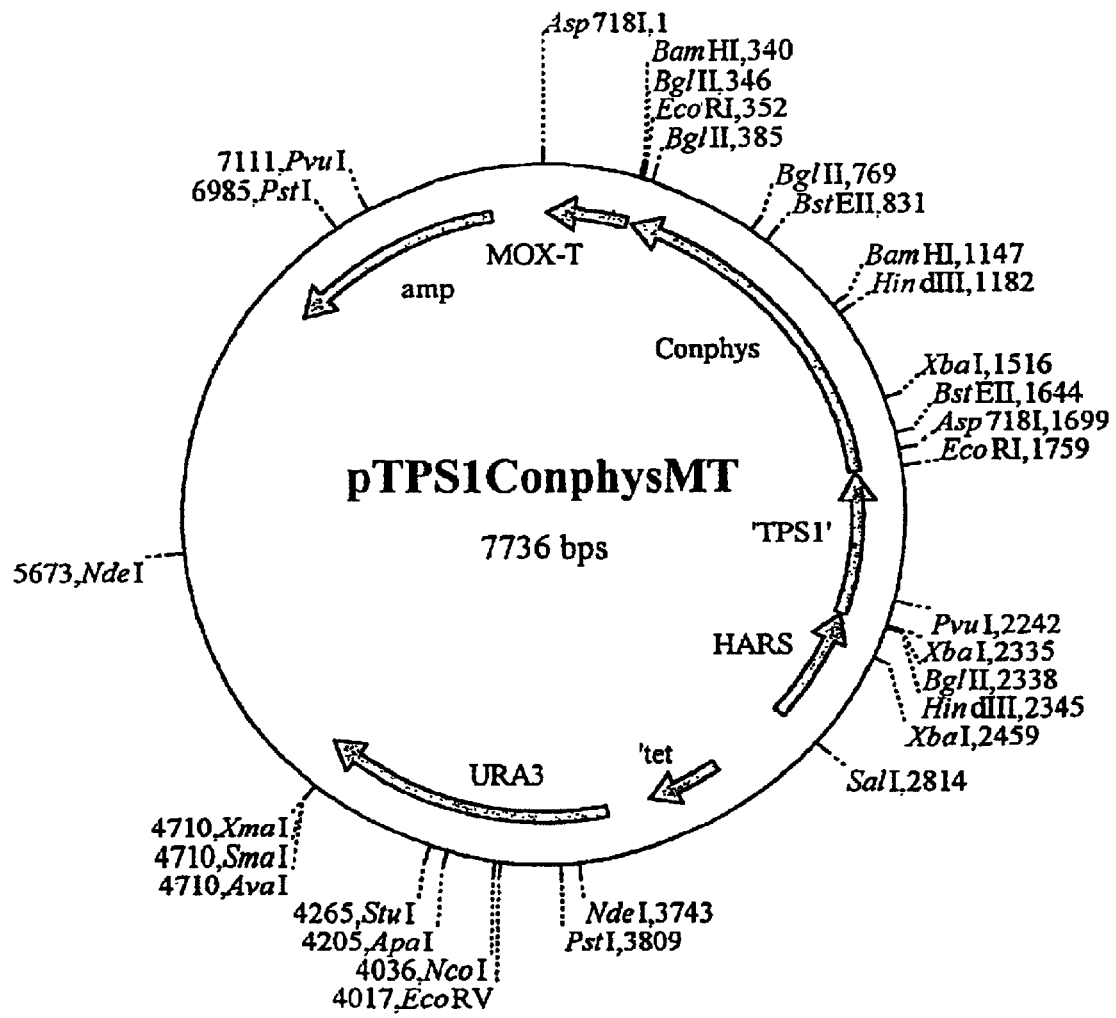
FIG. 11 shows the plasmid pTPS1ConphysMT used in Example 4. MOX-T=MOX terminator, Conphys=Conphys3 gene, TPS1=TPS1 promoter of *Hansenula polymorpha*, HARS=*H. polymorpha* Autonomously Replicating Sequences, tet=tetracycline-resistance gene, URA3=URA3 from *S. cerevisiae*, amp=ampicillin-resistance gene

Comparative Expression of a Phytase Gene Under the Control of the FMD and the TPS1 Promoter Recombinant strains were generated by transformation with the vectors pTPS1ConphysMT and pFMTConphysMT in accordance with standard procedures. With the exception of the promoter element in the expression cassette, the two vectors employed for transformation are identical. The heat-inducible promoter contained in pTPS1ConphysMT is the fragment corresponding to the sequence between nucleotides 228 and 792 in SEQ ID NO:1, the 3' terminus of which possesses an EcoRI restriction site (referred to below as the TPS1 promoter), whereas pFMTConPhysMT contains the FMD promoter. The plasmid map and the nucleotide sequence of the vector pTPS1ConphysMT are shown in FIG. 11. A mutein of a phytase was used as the reporter gene.

In this study, the TPS1 promoter was compared with the promoter most widely used to date, the FMD promoter. Use of the TPS1 promoter resulted in slightly increased expression values at 37° C. when compared to the FMD promoter. An expression two to three times higher than that observed with the FMD promoter was observed at 40° C. and 44° C. when the TPS1 promoter was employed.

BIBLIOGRAPHY

Bradford, M. M. (1976) A rapid and sensitive method for the quantitation of microgram quantities of protein utilizing the principle of protein-dye binding. *Anal Biochem* 72: 248-254.

Devereux, J., Haeberli, P. and Smithies, O. (1984) A comparative set of sequence analysis programs for the VAX. *Nucl Acids Res* 12: 387–395.

De Virgilio, C., Bürckert, N., Boller, T. and Wiemken, A. (1991) A method to study the rapid phosphorylation-related modulation of neutral trehalase activity by temperature shifts in yeast. *FEBS Lett* 291: 355–358.

Faber, K. N., Swaving, G. J., Faber, F., Ab, G., Harder, W., Veenhuis, M. and Haima, P. (1992) Chromosomal targeting of replicating plasmids in the yeast *Hansenula polymorpha*. *J Gen Microbiol* 138: 2405–2416.

Gatzke, R., Weydemann, U., Janowicz, Z. A. & Hollenberg, C. P. (1995) Stable multicopy integration of vector sequences in *Hansenula polymorpha*. *Appl. Microbiol. Biotechnol* 43, 844–849.)

Hottiger, T., Schmutz, P. and Wiemken, A. (1987) Heat-induced accumulation and futile cycling of trehalose in *Saccharomyces cerevisiae*. *J Bacteriol* 169: 5518–5522.

Huxley, C., Green, E. D. and Dunham I. (1990) Rapid assessment of *Saccharomyces cerevisiae* mating type by PCR. *Trends Genet* 6 (8): p. 236.

Laemmli, U. K. (1970) Cleavage of structural proteins during the assembly of the head of bacteriophage T4. *Nature* 227:680–685.

Levine, D. W. and Cooney, C. L. (1973) Isolation and characterization of a thermotolerant methanol-utilizing yeast. *Appl Microbiol* 26: 982–990.

Parrou, J. L. and François, J. (1997) A simplified procedure for a rapid and reliable assay of both glycogen and trehalose in whole yeast cells. *Anal Biochem* 248: 186–188.

Peterson, G. C. (1977) A simplification of the protein assay method of Lowry et al. which is more generally applicable. *Anal Biochem* 83: 346–356.

Piper, P. W. (1994) Measurement of transcription. In: *Molecular Genetics of yeast. A practical approach*, J. R. Johnston (ed.). IRL Press, Oxford.

Sambrook, J., Fritsch, E. F. and Maniatis, T. (1989) *Molecular Cloning: A Laboratory Manual.* Second edition. Cold Spring Harbor Laboratory Press, Cold Spring Harbor.

Weydemann U, Keup P, Piontek M, Strasser A W M, Schweden J, Gellissen G, Janowicz ZA (1995) High-level secretion of hirudin by *Hansenula polymorpha*— authentic processing of three different preprohirudins. *Appl Microbiol Biotechnol* 44:844–849

What is claimed is:

1. An isolated nucleic acid molecule comprising a heat-inducible promoter wherein the promoter is selected from the group consisting of:
    (a) a nucleic acid sequence comprising the promoter sequence of a *Hansenula polymorpha* gene encoding a protein having trehalose-6-phosphate synthase activity;
    (b) a nucleic acid having the sequence set forth in SEQ ID NO:1;
    (c) a nucleic acid which hybridizes, under stringent hybridization conditions, with the complementary strand of the nucleic acid set forth in one of (a) or (b), wherein said stringent hybridization conditions comprise (i) incubation of said nucleic acid set forth in one of (a) or (b) in 7% sodium dodecyl sulfate, 1% bovine serum albumin, 1 mM ethylenediaminetetraacetic acid, in 250 mM sodium phosphate buffer at pH 7.2 at 65° C. overnight, followed by washing with sodium chloride/sodium citrate buffer pH 7.0 (2×SSC), 0.1% sodium dodecyl sulfate or (ii) incubation of said nucleic acid set forth in one of (a) or (b) in 2×SSC at 68° C.;
    (d) a fragment of one of the nucleic acids set forth in any one of claims (a) to (c) which retains the function of the heat-inducible promoter, wherein said fragment is selected from the group consisting of the sequence from nucleotide 228 to nucleotide 792 in SEQ ID NO:1, the sequence from nucleotide 492 to nucleotide 792 in SEQ ID NO:1, and the sequence from nucleotide 627 to nucleotide 713 in SEQ ID NO:1;
    (e) a combination of a plurality of the nucleic acids set forth in any one of (a) to (d), wherein the sequences of each of the nucleic acids may be different or the same; and
    (f) a nucleic acid molecule having a sequence complementary to the sequence of one of the nucleic acids indicated in (a) to (e),
    wherein the nucleic acid molecule does not consist of the promoter sequence of the trehalose-6-phosphate synthase gene of *Saccharomyces cerevisiae* or *Schizosaccharomyces pombe*.

2. The isolated nucleic acid of claim 1, wherein the nucleic acid molecule comprises at least one heat shock element having the sequence NGAANNNNNNNGAAN (SEQ ID NO:2) or the complementary sequence thereof, wherein the nucleotides denoted by N may be any one of A, T, C or G.

3. The isolated nucleic acid of claim 2, wherein the nucleic acid molecule comprises at least one heat shock element having the sequence NGAANNBWMNNNGAAN (SEQ ID NO:3) or the complementary sequence thereof, wherein B is G, C, or T, W is A or T, and M is C or A.

4. The isolated nucleic acid of claim 2, wherein the heat shock element is selected from TGAAGCCTCTTGAAA (SEQ ID NO:4), TGAATATAAAGGAAA (SEQ ID NO:5), the complementary sequences thereof, and any combination thereof, wherein when two or more heat shock elements are present, each element may have the same or different sequences.

5. The isolated nucleic acid of claim 4, wherein the nucleic acid molecule comprises at least two heat shock elements having different sequences.

6. The isolated nucleic acid of claim 1, wherein the nucleic acid does not contain a Stress Responsive Element (an STRE element) having the sequence CCCCT or AGGGG.

7. The isolated nucleic acid of claim 1, wherein the nucleic acid molecule further comprises at least one nucleic acid sequence encoding a heterologous gene under the transcriptional control of the heat-inducible promoter.

8. The isolated nucleic acid of claim 1, further comprising a nucleic acid sequence under the control of the promoter, the nucleic acid under control of the promoter being selected from the group consisting of:
    (a) a nucleic acid sequence which encodes a polypeptide having the amino acid sequence of the trehalose-6-phosphate synthase of *Hansenula polymorpha;*
    (b) the nucleic acid sequence of SEQ ID NO:6;
    (c) a nucleic acid sequence comprising SEQ ID NO:6;
    (d) a nucleic acid sequence which encodes a polypeptide having the amino acid sequence indicated in SEQ ID NO:7,
    (e) a nucleic acid sequence which encodes a polypeptide having an amino acid sequence comprising SEQ ID NO:7.

9. A non-naturally occurring host cell containing the isolated nucleic acid of claim 1, the host cell being a prokaryotic or eukaryotic cell.

10. The host cell of claim 9, wherein the eukaryotic cell is a fungal cell.

11. The host cell of claim 10, wherein the fungal cell is a yeast cell.

12. The host cell of claim 11, wherein the yeast cell is *Hansenula polymorpha*.

13. An expression vector comprising at least one nucleic acid molecule of claim 1.

14. A kit, comprising:
    (a) the expression vector of claim 13, which is suitable for having cloned into it a nucleic acid which encodes a recombinant protein; and
    (b) a host cell suitable for induction of the heat-inducible promoter and for production of the recombinant protein.

15. A method for producing a protein comprising:
    (a) cloning at least one nucleic acid which encodes a recombinant protein into the expression vector of claim 13, wherein the nucleic acid encoding the recombinant protein is under the transcriptional control of the heat-inducible promoter;
    (b) introducing the expression vector obtained in (a) into a host cell suitable for induction of the heat-inducible promoter and for production of the recombinant protein;
    (c) cultivating the host cell obtained in (b);
    (d) inducing the heat-inducible promoter to express the protein.

16. The isolated nucleic acid of claim 4, wherein the nucleic acid does not contain an STRE element having the sequence CCCCT or AGGGG.

17. The isolated nucleic acid of claim 4, wherein the nucleic acid molecule further comprises at least one nucleic acid sequence encoding a heterologous gene under the transcriptional control of the heat-inducible promoter.

18. A non-naturally occurring host cell containing the isolated nucleic acid of claim 4, the host cell being a prokaryotic or eukaryotic cell.

19. An expression vector comprising at least one isolated nucleic acid molecule of claim 4.

20. A kit, comprising:
    (a) the expression vector of claim 19, which is suitable for having cloned into it a nucleic acid which encodes a recombinant protein; and
    (b) a host cell suitable for induction of the heat-inducible promoter and for production of the recombinant protein.

21. A method of expressing a protein comprising:
    (a) cloning at least one nucleic acid which encodes a recombinant protein into the expression vector of claim 19, wherein the nucleic acid encoding the recombinant protein is under the transcriptional control of the heat-inducible promoter;
    (b) introducing the expression vector obtained in (a) into a host cell suitable for induction of the heat-inducible promoter and for the production of the recombinant protein;
    (c) cultivating the host cell obtained in (b); and
    (d) inducing the heat-inducible promoter to express the protein.

* * * * *

SEQUENCE LISTING

```
<160> NUMBER OF SEQ ID NOS: 33

<210> SEQ ID NO 1
<211> LENGTH: 792
<212> TYPE: DNA
<213> ORGANISM: Hansenula polymorpha

<400> SEQUENCE: 1
cttaaatacc acaataggaa aattatcaat aaagcttttc ggatttcatt acgttatatc      60
gcaaaaaaat agtcgagctt tctgaaccgt tcgttaataa aaaaatagtt ttttcagatt     120
tctatgtgag gcagtcacga tagaattcca tcgaactcgt cagcgccaaa tgtgaatgcg     180
gctttcaaaa gctttgtcga atttgggatg ggaatccatg aatcgaagat gtcaaaatgg     240
gggatcacaa aagtacactc acgaggaaaa tcaaaacctt ctcgtacctt taacacatac     300
ggaaatgatc gatcgatttg agaagattcc tcaatgattt tcgtcatata taggtatctg     360
aggtatttat ggaccgattc gtaataacat catatacatc gcgctttgtc cctgtcccag     420
agatttcgat gaaaaaagcg aattttattc taatatttga agcatgccaa acatgggca      480 gttgatttgt gtgagggtaa aatatcatga attgcaccca tcaaatgcag caagatattg     540
accaatccta taatagaaaa cagacttacc acaaatagat tgtgatgacg atattatgaa     600
tctccagatg aaaggctcga aagctatgaa gcctcttgaa acttttcatg gtgagataat     660
attttcgaaa tttccacgaa cttctaaaac gcaattattg aatataaagg aaaaataata     720
tttccatata gcaagcaaat caagctgcac tcctcatcct taaaactaat aaatcttacc     780
catttgatac ca                                                         792

<210> SEQ ID NO 2
<211> LENGTH: 15
<212> TYPE: DNA
<213> ORGANISM: Artificial Sequence
<220> FEATURE:
<223> OTHER INFORMATION: Consensus sequence for a heat shock element
<220> FEATURE:
<221> NAME/KEY: misc_feature
<222> LOCATION: (1)..(15)
<223> OTHER INFORMATION: n may be a,c,t, or g

<400> SEQUENCE: 2
ngaannnnnn ngaan                                                       15

<210> SEQ ID NO 3
<211> LENGTH: 15
<212> TYPE: DNA
<213> ORGANISM: Artificial Sequence
<220> FEATURE:
<223> OTHER INFORMATION: Special embodiment of the heat shock element
```

-continued

```
<220> FEATURE:
<221> NAME/KEY: misc_feature
<222> LOCATION: (1)..(15)
<223> OTHER INFORMATION: n is a, c, t,or g; b is g, c, or t; w is a or
      t; and m is c or a

<400> SEQUENCE: 3
ngaannbwmn ngaan                                                      15

<210> SEQ ID NO 4
<211> LENGTH: 15
<212> TYPE: DNA
<213> ORGANISM: Artificial Sequence
<220> FEATURE:
<223> OTHER INFORMATION: Nucleic acid sequence of a heat shock element

<400> SEQUENCE: 4
tgaagcctct tgaaa                                                      15

<210> SEQ ID NO 5
<211> LENGTH: 15
<212> TYPE: DNA
<213> ORGANISM: Artificial Sequence
<220> FEATURE:
<223> OTHER INFORMATION: Nucleic acid sequence of a heat shock element

<400> SEQUENCE: 5
tgaatataaa ggaaa                                                      15

<210> SEQ ID NO 6
<211> LENGTH: 1903
<212> TYPE: DNA
<213> ORGANISM: Hansenula polymorpha

<400> SEQUENCE: 6
atggtcaaag gtaatgttat agtggtttca aatagaatcc cagtcactat taagaagact      60
gaagatgatg aaaatggaaa atcaagatac gactatacaa tgtcatcagg cggattagtg     120
acggcattac aagggctcaa aaatccattt cgatggtttg gatggcctgg gatgtctgtt     180
gatagcgaac agggacgaca aactgtcgag cgggatttga aggaaaagtt caattgttat     240
ccgatatggt taagtgacga aattgcagac ttacattata acggctttag caattctata     300 cttttggccat tgttccacta tcacccaggg gagatgaatt tgatgaaat tgcttgggcc      360 gcttatttgg aagcaaataa actgttttgc caaacgatct taaggagat aaaagacggg       420 gacgttatct gggtacatga ttatcatctc atgttgttgc cttcactgct aagagaccaa     480
cttaatagta agggctacc gaatgtcaaa attggctttt tccttcatac tcctttcct       540 tcaagcgaaa tatacaggat acttcctgta aggaaagaaa ttctcgaagg agtgcttagt     600
tgtgatttga taggttttcca cacctatgat tatgtccgtc acttctcttag ttcggttgaa    660 agaatattga aattgcgaac gagcccacaa ggtgttgtct ataatgatag acaggtgact    720
gtaagtgctt atccgattgg cattgacgtt gacaaattct tgaatggtct taagactgat    780
gaggtcaaaa gcaggataaa acagctggaa accagatttg gtaaagattg taaacttatt    840
attggggtgg acaggctgga ttacatcaaa ggtgtacctc aaaaactcca cgcgtttgaa    900
attttcttgg agagacaccc tgagtggatt ggaaagttg ttttgataca ggtggctgtc    960
ccctcacgag gggacgttga agaatatcaa tctttgaggg cagctgtaaa tgagctagtg    1020
ggaagaatca atggtagatt tggtaccgtc gaatttgttc ctatccattt ccttcataaa   1080
agcgtgaact tccaagagct gatatctgtc tacgctgcta gtgatgtttg tgtagtgtca   1140
```

```
tcgacacggg acggaatgaa tttggtcagt tatgaataca ttgcttgtca acaagatcga    1200
aagggatctc tagtactaag tgaatttgcg ggagctgctc agtcattaaa tggcgctctc    1260
gtagtgaatc catggaatac agaagaactc agtgaagcta tttacgaagg cttgatcatg    1320
agtgaagaga aaggagggg caattttcag aagatgttca agtacattga aaatatact      1380 gcaagttatt ggggagagaa ctttgtgaaa gaattgacga gagtgtgatt actgtggttt    1440
gcaggttaat ttgaaatgtt cacttgtact tgaagaattt tatattatat acatgttata    1500 catcaataggg ataaaaatta agtagacaaa gttatcattt tgtttgggctg taaaaattga   1560 acgataacaa tatatttgac aaaattaatt tgatctaatt gagctggagg gcgtaatata    1620 tttggttttcc tgaatcatct tgtagatcac aatatgggc agcttctttc gcagccgatc    1680
acagagaaac acatcacact tgtccaacat gatcacatat cgcattcaat cggggaaatg    1740
caaggataca ggttgaccat ggaagacgcg ttctgtgatt tgaacgaaag aatattcgtg    1800
acggaagagg gacttgacat cagaaaacaa gacgagaata cagagggtga tctggagtct    1860
cttcaaatta acatttatgg tgtctttgac ggacatggcg gtt                      1903
```

```
<210> SEQ ID NO 7
<211> LENGTH: 475
<212> TYPE: PRT
<213> ORGANISM: Hansenula polymorpha

<400> SEQUENCE: 7

Met Val Lys Gly Asn Val Ile Val Ser Asn Arg Ile Pro Val Thr
  1               5                  10                  15

Ile Lys Lys Thr Glu Asp Asp Glu Asn Gly Lys Ser Arg Tyr Asp Tyr
             20                  25                  30

Thr Met Ser Ser Gly Gly Leu Val Thr Ala Leu Gln Gly Leu Lys Asn
         35                  40                  45

Pro Phe Arg Trp Phe Gly Trp Pro Gly Met Ser Val Asp Ser Glu Gln
     50                  55                  60

Gly Arg Gln Thr Val Glu Arg Asp Leu Lys Glu Lys Phe Asn Cys Tyr
 65                  70                  75                  80

Pro Ile Trp Leu Ser Asp Glu Ile Ala Asp Leu His Tyr Asn Gly Phe
                 85                  90                  95

Ser Asn Ser Ile Leu Trp Pro Leu Phe His Tyr Pro Gly Glu Met
            100                 105                 110

Asn Phe Asp Glu Ile Ala Trp Ala Ala Tyr Leu Glu Ala Asn Lys Leu
        115                 120                 125

Phe Cys Gln Thr Ile Leu Lys Glu Ile Lys Asp Gly Asp Val Ile Trp
    130                 135                 140

Val His Asp Tyr His Leu Met Leu Leu Pro Ser Leu Leu Arg Asp Gln
145                 150                 155                 160

Leu Asn Ser Lys Gly Leu Pro Asn Val Lys Ile Gly Phe Phe Leu His
                165                 170                 175

Thr Pro Phe Pro Ser Ser Glu Ile Tyr Arg Ile Leu Pro Val Arg Lys
            180                 185                 190

Glu Ile Leu Glu Gly Val Leu Ser Cys Asp Leu Ile Gly Phe His Thr
        195                 200                 205

Tyr Asp Tyr Val Arg His Phe Leu Ser Ser Val Glu Arg Ile Leu Lys
    210                 215                 220

Leu Arg Thr Ser Pro Gln Gly Val Tyr Asn Asp Arg Gln Val Thr
225                 230                 235                 240
```

```
Val Ser Ala Tyr Pro Ile Gly Ile Asp Val Asp Lys Phe Leu Asn Gly
                245                 250                 255

Leu Lys Thr Asp Glu Val Lys Ser Arg Ile Lys Gln Leu Glu Thr Arg
            260                 265                 270

Phe Gly Lys Asp Cys Lys Leu Ile Ile Gly Val Asp Arg Leu Asp Tyr
        275                 280                 285

Ile Lys Gly Val Pro Gln Lys Leu His Ala Phe Glu Ile Phe Leu Glu
    290                 295                 300

Arg His Pro Glu Trp Ile Gly Lys Val Val Leu Ile Gln Val Ala Val
305                 310                 315                 320

Pro Ser Arg Gly Asp Val Glu Glu Tyr Gln Ser Leu Arg Ala Ala Val
                325                 330                 335

Asn Glu Leu Val Gly Arg Ile Asn Gly Arg Phe Gly Thr Val Glu Phe
            340                 345                 350

Val Pro Ile His Phe Leu His Lys Ser Val Asn Phe Gln Glu Leu Ile
        355                 360                 365

Ser Val Tyr Ala Ala Ser Asp Val Cys Val Val Ser Ser Thr Arg Asp
    370                 375                 380

Gly Met Asn Leu Val Ser Tyr Glu Tyr Ile Ala Cys Gln Gln Asp Arg
385                 390                 395                 400

Lys Gly Ser Leu Val Leu Ser Glu Phe Ala Gly Ala Ala Gln Ser Leu
                405                 410                 415

Asn Gly Ala Leu Val Val Asn Pro Trp Asn Thr Glu Glu Leu Ser Glu
            420                 425                 430

Ala Ile Tyr Glu Gly Leu Ile Met Ser Glu Glu Lys Arg Arg Gly Asn
        435                 440                 445

Phe Gln Lys Met Phe Lys Tyr Ile Glu Lys Tyr Thr Ala Ser Tyr Trp
    450                 455                 460

Gly Glu Asn Phe Val Lys Glu Leu Thr Arg Val
465                 470                 475

<210> SEQ ID NO 8
<211> LENGTH: 2695
<212> TYPE: DNA
<213> ORGANISM: Hansenula polymorpha

<400> SEQUENCE: 8
cttaaatacc acaataggaa aattatcaat aaagcttttc ggatttcatt acgttatatc      60
gcaaaaaaat agtcgagctt tctgaaccgt tcgttaataa aaaaatagtt ttttcagatt     120
tctatgtgag gcagtcacga tagaattcca tcgaactcgt cagcgccaaa tgtgaatgcg     180
gctttcaaaa gctttgtcga atttgggatg ggaatccatg aatcgaagat gtcaaaatgg     240
gggatcacaa agtacactc acgaggaaaa tcaaaacctt ctcgtacctt aacacatac       300 ggaaatgatc gatcgatttg agaagattcc tcaatgattt tcgtcatata taggtatctg     360
aggtatttat ggaccgattc gtaataacat catatacatc gcgctttgtc cctgtcccag     420
agatttcgat gaaaaagcg aattttattc taatatttga agcatgccaa acatggggca     480
gttgatttgt gtgagggtaa aatatcatga attgcaccca tcaaatgcag caagatattg     540
accaatccta aatagaaaaa cagacttacc acaaatagat tgtgatgacg atattatgaa     600
tctccagatg aaaggctcga aagctatgaa gcctcttgaa acttttcatg gtgagataat     660
attttcgaaa tttccacgaa cttctaaaac gcaattattg aatataaagg aaaaataata     720
tttccatata gcaagcaaat caagctgcac tcctcatcct taaaactaat aaatcttacc     780
```

```
catttgatac caatggtcaa aggtaatgtt atagtggttt caaatagaat cccagtcact      840
attaagaaga ctgaagatga tgaaaatgga aaatcaagat acgactatac aatgtcatca      900
ggcggattag tgacggcatt acaagggctc aaaaatccat ttcgatggtt tggatggcct      960
gggatgtctg ttgatagcga acagggacga caaactgtcg agcgggattt gaaggaaaag     1020
ttcaattgtt atccgatatg gttaagtgac gaaattgcag acttacatta taacggcttt     1080
agcaattcta tactttggcc attgttccac tatcacccag gggagatgaa ttttgatgaa     1140
attgcttggg ccgcttattt ggaagcaaat aaactgtttt gccaaacgat cttaaaggag     1200
ataaaagacg gggacgttat ctgggtacat gattatcatc tcatgttgtt gccttcactg     1260
ctaagagacc aacttaatag taaggggcta ccgaatgtca aaattggctt tttccttcat     1320
actccttttc cttcaagcga aatatacagg atacttcctg taaggaaaga aattctcgaa     1380
ggagtgctta gttgtgattt gataggtttc cacacctatg attatgtccg tcactttctt     1440
agttcggttg aaagaatatt gaaattgcga acgagcccac aaggtgttgt ctataatgat     1500
agacaggtga ctgtaagtgc ttatccgatt ggcattgacg ttgacaaatt cttgaatggt     1560
cttaagactg atgaggtcaa agcaggata aaacagctgg aaaccagatt tggtaaagat     1620
tgtaaactta ttattggggt ggacaggctg gattacatca aaggtgtacc tcaaaaactc     1680
cacgcgtttg aaattttctt ggagagacac cctgagtgga ttggaaaagt tgttttgata     1740
caggtggctg tccccctcacg agggacgtt gaagaatatc aatctttgag ggcagctgta     1800
aatgagctag tgggaagaat caatggtaga tttggtaccg tcgaatttgt tcctatccat     1860
ttccttcata aaagcgtgaa cttccaagag ctgatatctg tctacgctgc tagtgatgtt     1920
tgtgtagtgt catcgacacg ggacggaatg aatttggtca gttatgaata cattgcttgt     1980
caacaagatc gaaagggatc tctagtacta agtgaatttg cgggagctgc tcagtcatta     2040
aatgcgcgctc tcgtagtgaa tccatggaat acagaagaac tcagtgaagc tatttacgaa     2100
ggcttgatca tgagtgaaga gaaaaggagg ggcaattttc agaagatgtt caagtacatt     2160
gagaaatata ctgcaagtta ttgggggagag aactttgtga agaattgac gagagtgtga     2220
ttactgtggt ttgcaggtta atttgaaatg ttcacttgta cttgaagaat tttatattat     2280
atacatgtta tacatcaata ggataaaaat taagtagaca aagttatcat tttgttgggc     2340
tgtaaaaatt gaacgataac aatatatttg acaaaattaa tttgatctaa ttgagctgga     2400
gggcgtaata tatttggttt cctgaatcat cttgtagatc acaatatggg gcagcttctt     2460
tcgcagccga tcacagagaa acacatcaca cttgtccaac atgatcacat atcgcattca     2520
atcggggaaa tgcaaggata caggttgacc atggaagacg cgttctgtga tttgaacgaa     2580
agaatattcg tgacggaaga gggacttgac atcagaaaac aagacgagaa tacagagggt     2640
gatctggagt ctcttcaaat taacatttat ggtgtctttg acggacatgg cggtt          2695
```

<210> SEQ ID NO 9
<211> LENGTH: 26
<212> TYPE: DNA
<213> ORGANISM: Artificial Sequence
<220> FEATURE:
<223> OTHER INFORMATION: PCR primer F1 (forward)
<220> FEATURE:
<221> NAME/KEY: misc_feature
<222> LOCATION: (1)..(26)
<223> OTHER INFORMATION: n is a, c, t, or g; v is a, c, or g; y is c or
      t;

<400> SEQUENCE: 9

```
tggccvytnt tccaytacca tccygg                                    26

<210> SEQ ID NO 10
<211> LENGTH: 24
<212> TYPE: DNA
<213> ORGANISM: Artificial Sequence
<220> FEATURE:
<223> OTHER INFORMATION: PCR primer R1 (backward)
<220> FEATURE:
<221> NAME/KEY: misc_feature
<222> LOCATION: (1)..(24)
<223> OTHER INFORMATION: r is a or g; b is  c, g, or t; y is c or
      t, h is a, c, or t

<400> SEQUENCE: 10
ggcrtgbaay ttytghggha cacc                                      24

<210> SEQ ID NO 11
<211> LENGTH: 23
<212> TYPE: DNA
<213> ORGANISM: Artificial Sequence
<220> FEATURE:
<223> OTHER INFORMATION: Sequencing Primer F3 (forward)

<400> SEQUENCE: 11
ggaagcaaat aaactgtttt gcc                                       23

<210> SEQ ID NO 12
<211> LENGTH: 23
<212> TYPE: DNA
<213> ORGANISM: Artificial Sequence
<220> FEATURE:
<223> OTHER INFORMATION: Sequencing primer F4 (forward)

<400> SEQUENCE: 12
ctgtaagtgc ttatccgatt ggc                                       23

<210> SEQ ID NO 13
<211> LENGTH: 22
<212> TYPE: DNA
<213> ORGANISM: Artificial Sequence
<220> FEATURE:
<223> OTHER INFORMATION: Sequencing primer F6 (forward)

<400> SEQUENCE: 13
ggacgacaaa ctgtcgagcg gg                                        22

<210> SEQ ID NO 14
<211> LENGTH: 22
<212> TYPE: DNA
<213> ORGANISM: Artificial Sequence
<220> FEATURE:
<223> OTHER INFORMATION: Sequencing primer F7 (forward)

<400> SEQUENCE: 14
catactcctt ttccttcaag cg                                        22

<210> SEQ ID NO 15
<211> LENGTH: 21
<212> TYPE: DNA
<213> ORGANISM: Artificial Sequence
<220> FEATURE:
<223> OTHER INFORMATION: Sequencing primer F8 (forward)

<400> SEQUENCE: 15
aaagcgtgaa cttccaagag c                                         21
```

```
<210> SEQ ID NO 16
<211> LENGTH: 22
<212> TYPE: DNA
<213> ORGANISM: Artificial Sequence
<220> FEATURE:
<223> OTHER INFORMATION: Sequencing primer F9 (forward)

<400> SEQUENCE: 16
gcgtgtgatt actgtggttt gc                                                  22

<210> SEQ ID NO 17
<211> LENGTH: 26
<212> TYPE: DNA
<213> ORGANISM: Artificial Sequence
<220> FEATURE:
<223> OTHER INFORMATION: Sequencing primer F10 (forward)

<400> SEQUENCE: 17
ggtgagataa tattttcgaa atttcc                                              26

<210> SEQ ID NO 18
<211> LENGTH: 27
<212> TYPE: DNA
<213> ORGANISM: Artificial Sequence
<220> FEATURE:
<223> OTHER INFORMATION: Sequencing primer F11 (forward)

<400> SEQUENCE: 18
cccatcaaat gcagcaagat attgacc                                             27

<210> SEQ ID NO 19
<211> LENGTH: 21
<212> TYPE: DNA
<213> ORGANISM: Artificial Sequence
<220> FEATURE:
<223> OTHER INFORMATION: Sequencing primer F3 (backward)

<400> SEQUENCE: 19
ccattcaaga atttgtcaac g                                                   21

<210> SEQ ID NO 20
<211> LENGTH: 23
<212> TYPE: DNA
<213> ORGANISM: Artificial Sequence
<220> FEATURE:
<223> OTHER INFORMATION: Sequencing primer R4 (backward)

<400> SEQUENCE: 20
catgagatga taatcatgta ccc                                                 23

<210> SEQ ID NO 21
<211> LENGTH: 23
<212> TYPE: DNA
<213> ORGANISM: Artificial Sequence
<220> FEATURE:
<223> OTHER INFORMATION: Sequencing Primer R5 (backward)

<400> SEQUENCE: 21
caattttgac attcggtagc ccc                                                 23

<210> SEQ ID NO 22
<211> LENGTH: 22
<212> TYPE: DNA
<213> ORGANISM: Artificial Sequence
<220> FEATURE:
```

```
<223> OTHER INFORMATION: Sequencing primer R6 (backward)

<400> SEQUENCE: 22
gtaatgccgt cactaatccg cc                                        22

<210> SEQ ID NO 23
<211> LENGTH: 23
<212> TYPE: DNA
<213> ORGANISM: Artificial Sequence
<220> FEATURE:
<223> OTHER INFORMATION: Sequencing primer R7 (backward)

<400> SEQUENCE: 23
gaacatcttc tgaaaattgc ccc                                       23

<210> SEQ ID NO 24
<211> LENGTH: 21
<212> TYPE: DNA
<213> ORGANISM: Artificial Sequence
<220> FEATURE:
<223> OTHER INFORMATION: Sequencing primer R8 (backward)

<400> SEQUENCE: 24
ctagctcatt tacagctgcc c                                         21

<210> SEQ ID NO 25
<211> LENGTH: 25
<212> TYPE: DNA
<213> ORGANISM: Artificial Sequence
<220> FEATURE:
<223> OTHER INFORMATION: Sequencing primer R9 (backward)

<400> SEQUENCE: 25
catagctttc gagcctttca tctgg                                     25

<210> SEQ ID NO 26
<211> LENGTH: 24
<212> TYPE: DNA
<213> ORGANISM: Artificial Sequence
<220> FEATURE:
<223> OTHER INFORMATION: Sequencing primer Plasm. F (forward)

<400> SEQUENCE: 26
ggcgagcccg atcttcccca tcgg                                      24

<210> SEQ ID NO 27
<211> LENGTH: 26
<212> TYPE: DNA
<213> ORGANISM: Artificial Sequence
<220> FEATURE:
<223> OTHER INFORMATION: Sequencing primer  Plasm. R (backward)

<400> SEQUENCE: 27
ctgctcgctt cgctacttgg agccac                                    26

<210> SEQ ID NO 28
<211> LENGTH: 15
<212> TYPE: DNA
<213> ORGANISM: Saccharomyces cerevisiae
<220> FEATURE:
<221> NAME/KEY: misc_feature
<223> OTHER INFORMATION: Heat shock element

<400> SEQUENCE: 28
ggaacagaac aatcg                                                15
```

```
<210> SEQ ID NO 29
<211> LENGTH: 249
<212> TYPE: DNA
<213> ORGANISM: S. cerevisiae
<220> FEATURE:
<221> NAME/KEY: misc_feature
<223> OTHER INFORMATION: TPS1

<400> SEQUENCE: 29
agcgatgaaa tcgcagactt actctacaac tggttcagta attctattct atggccgtta      60
ttccattacc atcctggtga gatcaatttc gacgagaatg cgtggtcggc atacaacgag     120
gcaaaccaga cgttcaccaa cgagattgcg ttggtgtcga caggctggat tacatcaaag     180
gtgtgcctca gaagttgcac gccatggaag tgtttctgaa cgagcatcca gaatggaggg     240
gcaaggttg                                                             249

<210> SEQ ID NO 30
<211> LENGTH: 249
<212> TYPE: DNA
<213> ORGANISM: K. lactis
<220> FEATURE:
<221> NAME/KEY: misc_feature
<223> OTHER INFORMATION: TPS1

<400> SEQUENCE: 30
agtgacgaag ttgctgatct tcattacaac ggattttcca actctattct atggccattg      60
ttccattacc atcctggtga gatcactttc gatgacactg catggttggc gtacaacgag     120
gcaaatatgg cttttgccga tgaaattgaa ttggggtcga tcgtcttgat tacatcaaag     180
gtgttcctca gaagttacac gccttggaag tgttcctcgg tgcgcatcct gaatggattg     240
gtaaggtgg                                                             249

<210> SEQ ID NO 31
<211> LENGTH: 249
<212> TYPE: DNA
<213> ORGANISM: C. albicans
<220> FEATURE:
<221> NAME/KEY: misc_feature
<223> OTHER INFORMATION: TPS1

<400> SEQUENCE: 31
agtgatacga ttgctgattt acattataat gggttttcaa atagtatttt atggccactt      60
ttccattatc atcctgggga aatgaacttt gatgaaaatg catgggcagc atatattgaa     120
gccaataaga aatttgcatt ggaaatagtg ttggtgttga tagattagac tatatcaaag     180
gtgttccgca aaaattacat gcatttgaag tcttttttgaa tgaaaatccc gaatggattg     240
gcaaagtag                                                             249

<210> SEQ ID NO 32
<211> LENGTH: 249
<212> TYPE: DNA
<213> ORGANISM: S. pombe
<220> FEATURE:
<221> NAME/KEY: misc_feature
<223> OTHER INFORMATION: TPS1

<400> SEQUENCE: 32
gatgatgaga ctgccgaccg ccattacaac ggatttagta acagcattct ttggcccttg      60
ttccactacc atcctggtga aattaatttt gacgaggaaa attgggaggc ctatcgtgcg     120
gctaactacg cttttgccga ggccattgtg tgggtgtcga tcgtttggac tacattaagg     180
```

```
gtgttcccca aaaattccat gcctttgaag tgttcttaga acaataccct gaatgggttg      240
gaaaggtcg                                                             249

<210> SEQ ID NO 33
<211> LENGTH: 250
<212> TYPE: DNA
<213> ORGANISM: A. niger
<220> FEATURE:
<221> NAME/KEY: misc_feature
<223> OTHER INFORMATION: TPS1

<400> SEQUENCE: 33
ctgaaggcgc ttgcttgctg acggatatcc actgctcaca gactccattc tctggcccct      60
cttccattac catcccggtg agattacctt tgacgagtcc gcctgggaag catacaagga     120
ggccaaccgt cttttcgcca aagcggttgc gtgggtgtgg accgcctgga ttacatcaaa     180
ggtgtccccc agaagttaca tgcccttgag gtgttcctta gcgatcatcc ggagtgggtt     240
ggcaaggttg                                                            250
```